(12) United States Patent
Shue et al.

(10) Patent No.: US 7,303,550 B2
(45) Date of Patent: Dec. 4, 2007

(54) DISPOSABLE SYRINGE WITH A RETRACTABLE NEEDLE

(76) Inventors: Ming-Jeng Shue, No. 14, Lane 8, Chung-I St., Hsi Dist., Taichung City (TW); Deborah Huang, 7F, No. 5, Sec. 3, Liu-Chun E. St., Chung Dist., Taichung City (TW); Phillip Shue, No. 14, Lane 8, Chung-I St., Hsi Dist., Taichung City (TW)

( * ) Notice: Subject to any disclaimer, the term of this patent is extended or adjusted under 35 U.S.C. 154(b) by 262 days.

(21) Appl. No.: 10/975,784

(22) Filed: Oct. 28, 2004

(65) Prior Publication Data

US 2005/0277880 A1  Dec. 15, 2005

(30) Foreign Application Priority Data

Jun. 11, 2004  (TW) .............................. 93116875 A

(51) Int. Cl.
*A61M 5/32*  (2006.01)

(52) U.S. Cl. ...................... 604/197; 604/110; 604/192; 604/195; 604/240; 604/243

(58) Field of Classification Search ................ 604/110, 604/195, 197, 181, 187, 192, 240, 243
See application file for complete search history.

(56) References Cited

U.S. PATENT DOCUMENTS 5,716,341 A * 2/1998 Saito .......................... 604/110

* cited by examiner

*Primary Examiner*—Kevin C. Sirmons
*Assistant Examiner*—Laura C. Schell
(74) *Attorney, Agent, or Firm*—Ohlandt, Greeley, Ruggiero & Perle L.L.P.

(57) ABSTRACT

A disposable syringe includes a tubular needle seat inserted into a barrel for fixing a needle cannula. The needle seat has an axially extending cavity with a radially yieldable catch disposed therein. A plunger is movable in the barrel, and has an engaging head defining a rearwardly facing shoulder wall which is retained by the catch when the engaging head is extended into the cavity by a pushing force applied to the plunger. The barrel defines friction diminishing regions such that when the needle seat is moved past the friction diminishing regions to be placed to a disposal position, friction between the needle seat and the barrel is diminished, thereby facilitating a subsequent pulling action of the plunger for retracting the needle cannula into the barrel.

18 Claims, 29 Drawing Sheets

DISPOSABLE SYRINGE WITH A RETRACTABLE NEEDLE

CROSS-REFERENCE TO RELATED APPLICATION

This application claims priority of Taiwanese Application No. 093116875, filed on Jun. 11, 2004.

BACKGROUND OF THE INVENTION

1. Field of the Invention

This invention relates to a disposable syringe, more particularly to a disposable syringe with a friction diminishing means to facilitate retraction of a needle into a barrel for safe disposal.

2. Description of the Related Art

Conventional syringes, especially those with a sharp needle, have to be disposed safely after injection. Although a tip protector is used to shield the needle, the user is exposed to the risk of being stuck by the needle when sleeving the tip protector back on the syringe. There are many syringes with a retractable needle that is retracted into a barrel by pulling a plunger backward. However, it is desirable to improve the steady retraction movement of the needle and to reduce defective products during manufacture.

SUMMARY OF THE INVENTION

The object of the present invention is to provide a disposable syringe which permits steady and successful retraction of a needle, and which can reduce failure in production.

According to this invention, the disposable syringe includes a barrel, a tubular needle seat and a plunger. The barrel has an axially extending surrounding barrel wall which defines a passage with front and rear open ends. An inner wall surface of the surrounding barrel wall includes front and rear surface segments and an intermediate surface segment disposed therebetween. The intermediate surface segment has a retaining region axially distal from the front surface segment, and first and second friction diminishing regions respectively interposed between the retaining region and the front surface segment, and between the retaining region and the rear surface segment.

The tubular needle seat is insertable into the passage from the rear open end, and includes a front engaging portion in fluid-tight engagement with the front surface segment to fix a needle cannula, a retaining portion which is disposed rearwardly of the front engaging portion, and which is retained at the retaining region by virtue of a first frictional force when the needle seat is in a position of use, a rear engaging portion which extends rearwardly from the retaining portion to terminate at a rearwardly facing wall, and a surrounding sealing flange which extends from the rearwardly facing wall radially and outwardly to be in fluid-tight engagement with the rear surface segment, and which extends forwardly to terminate at a surrounding flange surface that is movable towards the second friction diminishing region. The rear engaging portion has an inner tubular wall surface defining a cavity which extends from the rearwardly facing wall to terminate at a ceiling wall. The ceiling wall has an axial hole which establishes a fluid communication between the needle cannula and the cavity. A radially yieldable catch is disposed on the inner tubular wall surface distal from the ceiling wall, and is yieldable radially and outwardly in response to a kinetic frictional force.

The plunger is movable in the passage, and has a front end wall, an engaging head opposite to the front end wall, and a neck interposed therebetween and of a dimension such that a rearwardly facing shoulder wall is formed between the engaging head and the neck. The kinetic frictional force is generated as a result of axial movement of the engaging head relative to the radially yieldable catch towards the ceiling wall. A deformable sealing member is sleeved on the engaging head and the neck, is in frictional engagement with the engaging head with a second frictional force, and is sealingly slidable relative to the rear surface segment.

In the position of use, the deformable sealing member is moved forward by virtue of forward movement of the plunger to abut against the rearwardly facing wall, while the engaging head is extended into the cavity.

When the plunger is to be placed in a disposal position, the engaging head is kept moving towards the ceiling wall by a pushing force which is applied to the plunger, and which, when the deformable sealing member is blocked by the rearwardly facing wall from moving with the engaging head, overcomes the second frictional force, thereby exposing the neck so as to permit the rearwardly facing shoulder wall to be forced to slip over the radially yieldable catch and to be prevented from moving rearwardly by the radially yieldable catch.

After the rearwardly facing shoulder wall has slipped over the radially yieldable catch, continued movement of the engaging head towards the ceiling wall, against the first frictional force, forces the retaining portion and the surrounding sealing flange to move into the first and second friction diminishing regions, respectively, so as to facilitate a subsequent pulling action of the plunger whereby the needle seat is brought towards the rear open end by virtue of the retaining engagement of the rearwardly facing shoulder wall and the radially yieldable catch, thereby retracting the needle cannula into the passage.

BRIEF DESCRIPTION OF THE DRAWINGS

Other features and advantages of the present invention will become apparent in the following detailed description of the preferred embodiments of the invention, with reference to the accompanying drawings, in which.

DETAILED DESCRIPTION OF THE PREFERRED EMBODIMENTS

Figure 1:
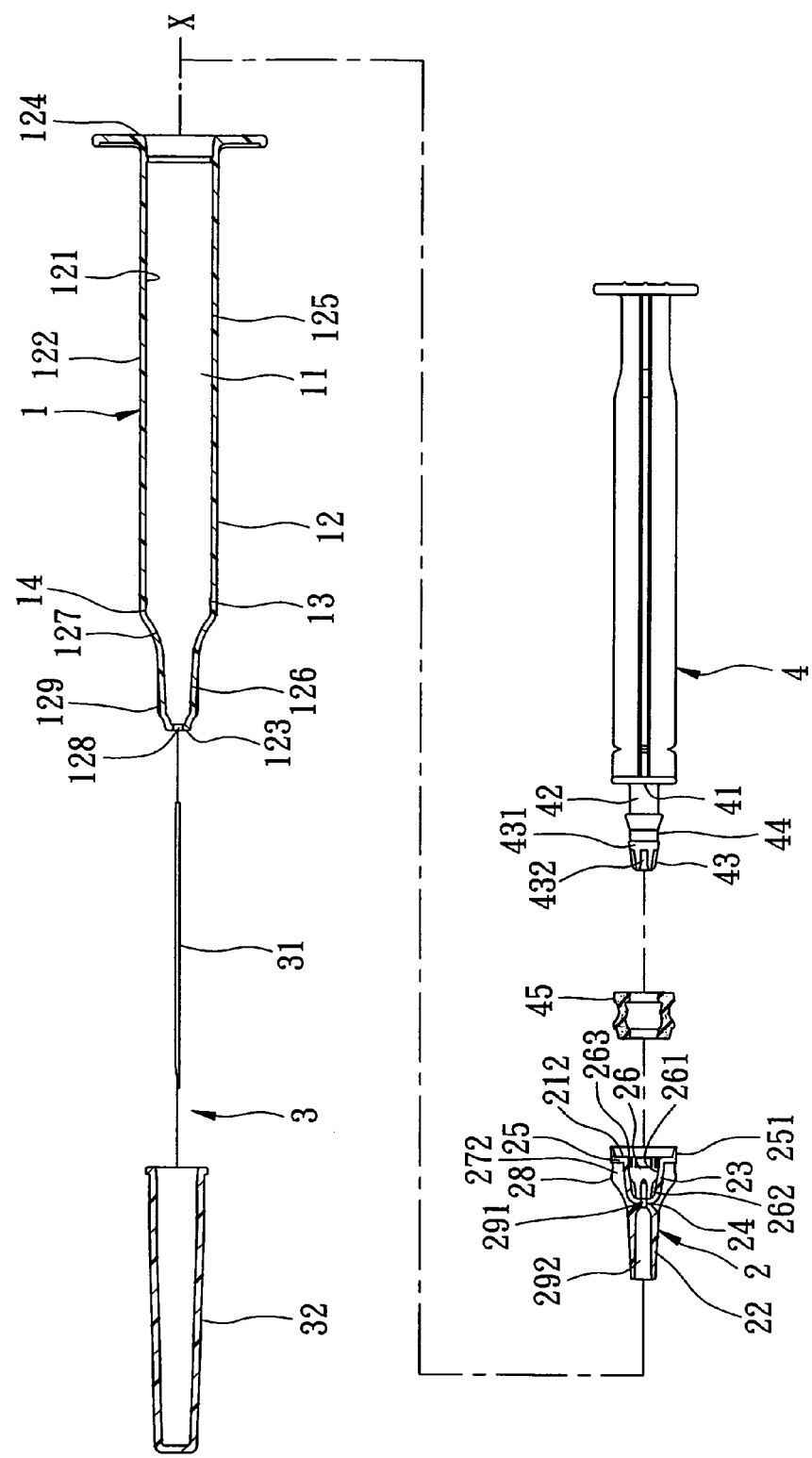
FIG. 1 is an exploded sectional view of the first preferred embodiment of a disposable syringe according to this invention.

Before the present invention is described in greater detail, it should be noted that same reference numerals have been used to denote like elements throughout the specification.

Figure 2:
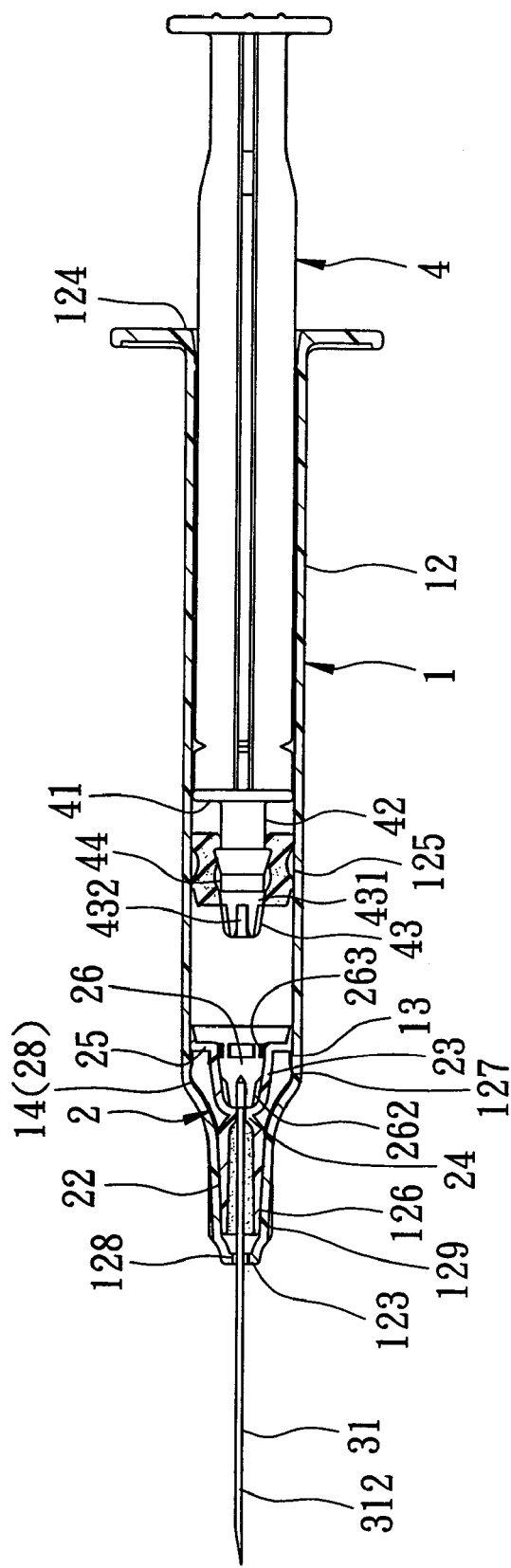
FIG. 2 is a sectional view of the first preferred embodiment in a state of use.
Figure 3:
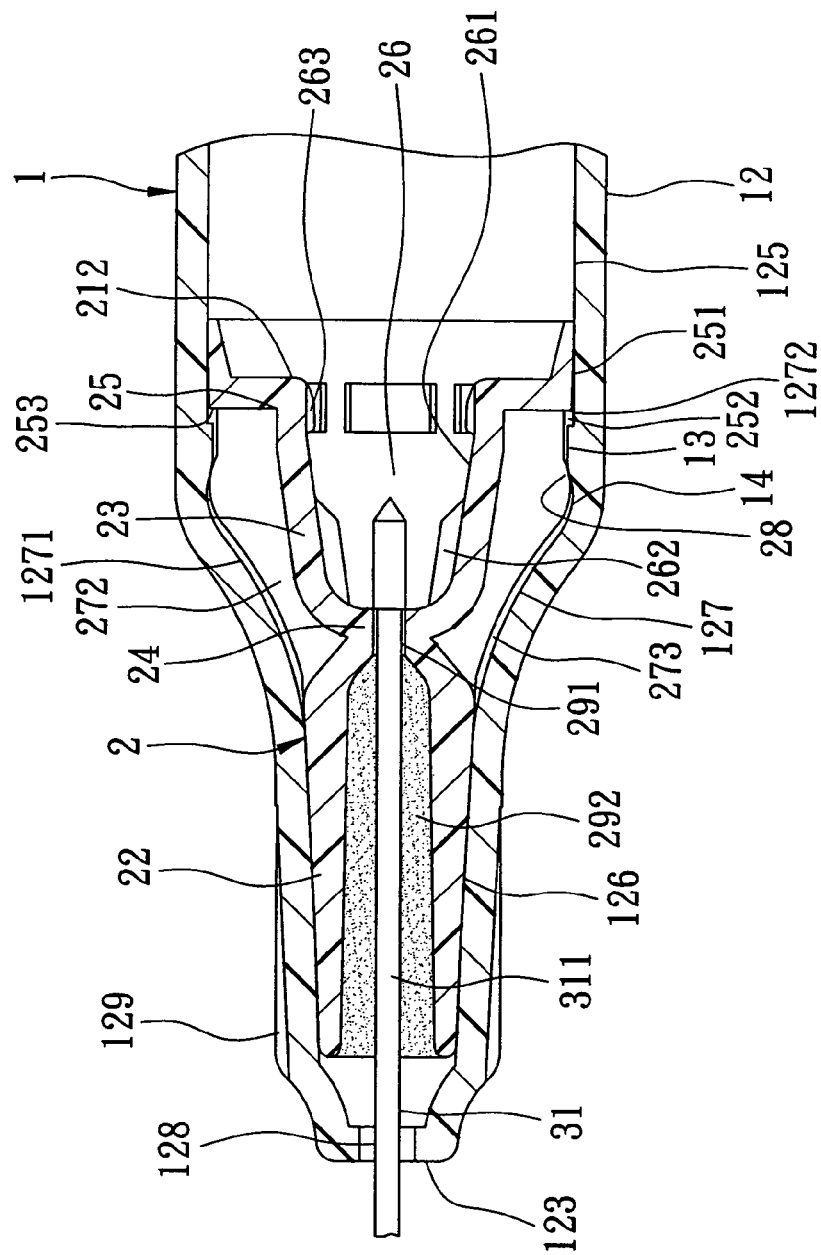
FIG. 3 is a fragmentary sectional view of the first preferred embodiment, showing a needle seat retained in a barrel.

Referring to FIGS. 1 to 3, the first preferred embodiment of a disposable syringe according to the present invention is shown to comprise a barrel 1, a tubular needle seat 2, a needle assembly 3 including a needle cannula 31 and a tip protector 32, and a plunger 4.

The barrel 1 has a surrounding barrel wall 12 which surrounds an axis (X) in a longitudinal direction and which defines a passage 11 therein that has front and rear open ends 123, 124 opposite to each other. The surrounding barrel wall 12 has inner and outer wall surfaces 121, 122. The inner wall surface 121 includes a smaller-diameter front surface segment 126 and a larger-diameter rear surface segment 125 proximate to the front and rear open ends 123, 124, respectively, and an intermediate surface segment 127 disposed therebetween and converging from the rear surface segment 125 to the front surface segment 126.

The intermediate surface segment 127 has a retaining region 14 which is axially distal from the front surface segment 126 and which extends radially and outwardly to form an annular recess 14. An annular shoulder abutment 13 is formed on the intermediate surface segment 127 rearwardly of the retaining region 14. Moreover, the intermediate surface segment 127 defines first and second friction diminishing regions 1271, 1272 which are respectively interposed between the retaining region 14 and the front surface segment 126, and between the retaining region 14 and the rear surface segment 125 to be described in greater detail hereinafter.

The outer wall surface 122 of the barrel 1 has a rib portion 129 extending in the longitudinal direction and disposed adjacent to the front open end 123. The tip protector 32 of the needle assembly 3 is disposed to sleeve on the outer wall surface 122 from the front open end 123, and is frictionally retained by the rib portion 129 for shielding the needle cannula 31.

The needle seat 2 is insertable into the passage 11 from the rear open end 124 to surround the axis (X). The needle seat 2 includes a front engaging portion 22, a retaining portion 23, a rear engaging portion 25, a surrounding sealing flange 251, a plurality of radially yieldable catches 263, and a plurality of axially extending ribs 262.

The front engaging portion 22 is configured to be in fluid-tight engagement with the front surface segment 126, and is disposed to fix the needle cannula 31 of the needle assembly 3 along the axis (X). Specifically, the front engaging portion 22 has a filling hole 292 filled with an adhesive to affix a secured segment 311 of the needle cannula 31 to the front engaging portion 22 (see FIG. 3). In this embodiment, the front surface segment 126 of the barrel 1 is configured to converge toward the front open end 123 to form a narrow opening 128 in the front open end 123 for passage of a sharp segment 312 of the needle cannula 31, thereby preventing removal of the needle seat 2 from the front open end 123.

The retaining portion 23 is disposed rearwardly of the front engaging portion 22, and is retained at the retaining region 14 by virtue of a first frictional force when the needle seat 2 is in a position of use. In particular, the retaining portion 23 has a plurality of fins 272 which are angularly displaced from one another about the axis (X), and which are spaced apart from the first diminishing region 1271 radially so as to form a first movement space 273 therebetween. Each fin 272 is configured such that a contour constituted by the fins 272 about the axis (X) serves as a protrusion 28. The protrusion 28 is retained in the annular recess 14 by virtue of the first frictional force.

The rear engaging portion 25 extends rearwardly from the retaining portion 23 to terminate at a rearwardly facing wall 212. The surrounding sealing flange 251 extends from the rearwardly facing wall 212 radially and outwardly to be in fluid-tight engagement with the rear surface segment 125, and extends forwardly to terminate at a surrounding flange surface 253. The surrounding flange surface 253 is spaced apart from the shoulder abutment 13 by the second friction diminishing region 1272 so as to form a second movement space 252 therebetween. Furthermore, the rear engaging portion 25 has an inner tubular wall surface 261 which surrounds the axis (X) to define a cavity 26 that extends from the rearwardly facing wall 212 towards the front engaging portion 22 and that terminates at a ceiling wall 24. The ceiling wall 24 has an axial hole 291 which is in fluid communication with the filling hole 292 to establish a fluid communication between the needle cannula 31 and the cavity 26.

The radially yieldable catches 263 and the axially extending ribs 262 are formed on the inner tubular wall surface 261 distal from and proximate to the ceiling wall 24, respectively, and are angularly displaced from one another about the axis (X). The radially yieldable catches 263 are yieldable radially and outwardly in response to a kinetic frictional force to be described in greater detail hereinafter.

The plunger 4 is disposed to be movable in the passage 11 along the rear surface segment 125, and has a front end wall 41, an engaging head 43 which is opposite to the front end wall 41 in the longitudinal direction and which has a plurality of axially extending grooves 432, a neck 44 which is interposed between the engaging head 43 and the front end wall 41, and which is of a dimension such that a rearwardly facing shoulder wall 431 is formed between the engaging head 43 and the neck 44, and such that the aforesaid kinetic frictional force is generated as a result of axial movement of the engaging head 43 relative to the radially yieldable catches 263 towards the ceiling wall 24, and an axially extending stem 42 which is interposed between the neck 44 and the front end wall 41. A deformable sealing member 45 is sleeved on the engaging head 43 and the neck 44, is in frictional engagement with the engaging head 43 with a second frictional force, and is sealingly slidable relative to the rear surface segment 125. Furthermore, the deformable sealing member 45 is spaced apart from the front end wall 41 so as to permit relative movement of the deformable sealing member 45 towards the front end wall 41 when a pushing force is applied to the plunger 4 to overcome the second frictional force to be described in greater detail hereinafter.

Figure 4:
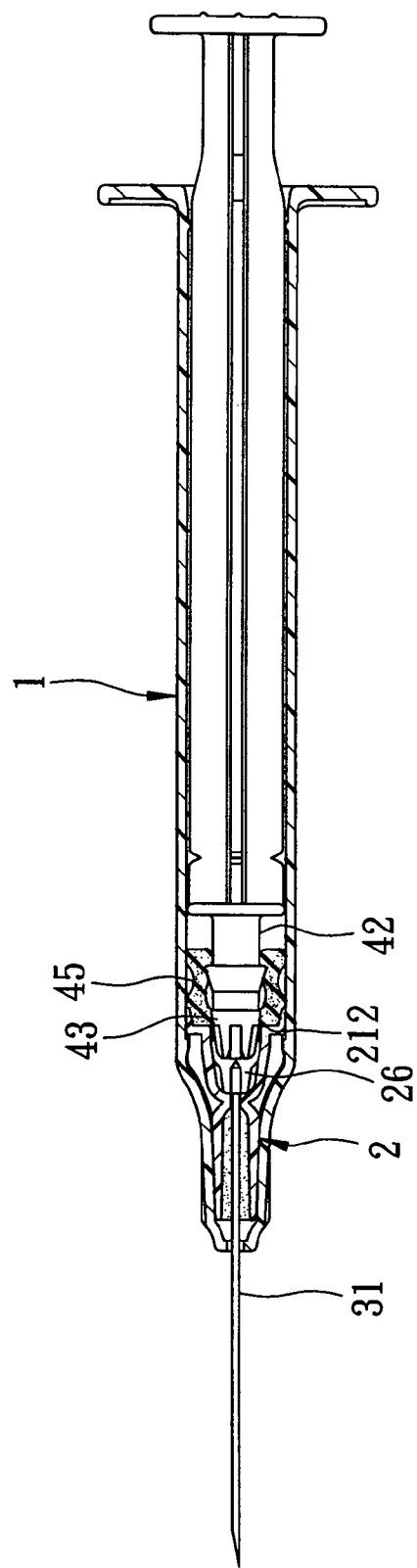
FIG. 4 is a sectional view of the first preferred embodiment in an injection completed state.

Referring to FIG. 4, in the position of use, i.e., during an injection procedure, as shown in FIG. 4, the deformable sealing member 45 is moved forward by virtue of forward movement of the plunger 4 to abut against the rearwardly facing wall 212, while the engaging head 43 extends into the cavity 26. The syringe is thus placed in an injection completed state.

Figure 5:
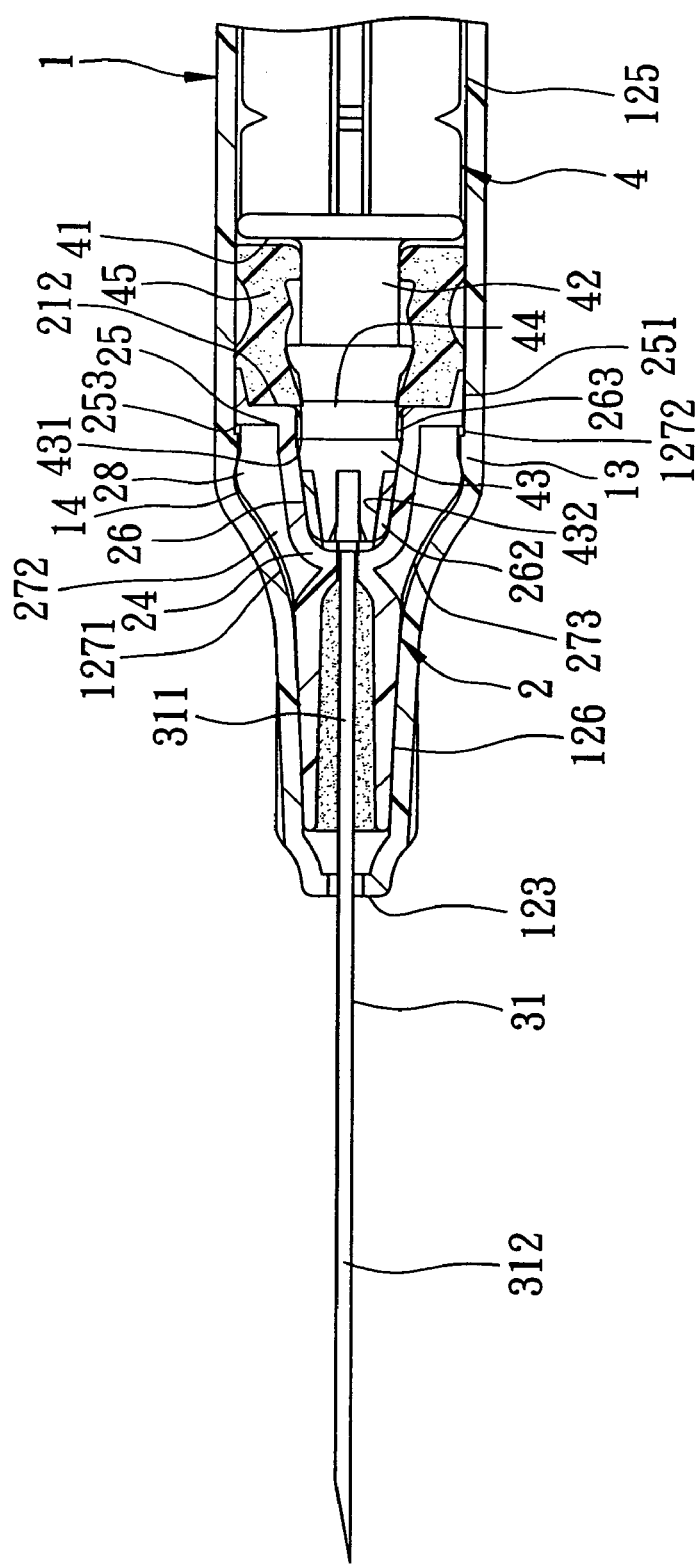
FIG. 5 is a fragmentary sectional view of the first preferred embodiment showing an engaging head of a plunger retained in a cavity of the needle seat.

Referring to FIG. 5, when the plunger 4 is to be placed in a disposal position, the engaging head 43 is kept moving towards the ceiling wall 24 by a pushing force which is applied to the plunger 4, and which, when the deformable sealing member 45 is blocked by the rearwardly facing wall 212 from moving with the engaging head 43 and is moved rearwardly towards the front end wall 41, overcomes the second frictional force, thereby exposing the neck 44 to permit the rearwardly facing shoulder wall 431 to be forced to slip over the radially yieldable catches 263 and to be retained thereby such that the rearwardly facing shoulder wall 431 is prevented from moving rearwardly. Meanwhile, the axially extending grooves 432 are brought to mate with the axially extending ribs 262 so as to put the needle seat 2 into splined engagement with the engaging head 43.

Figure 6:
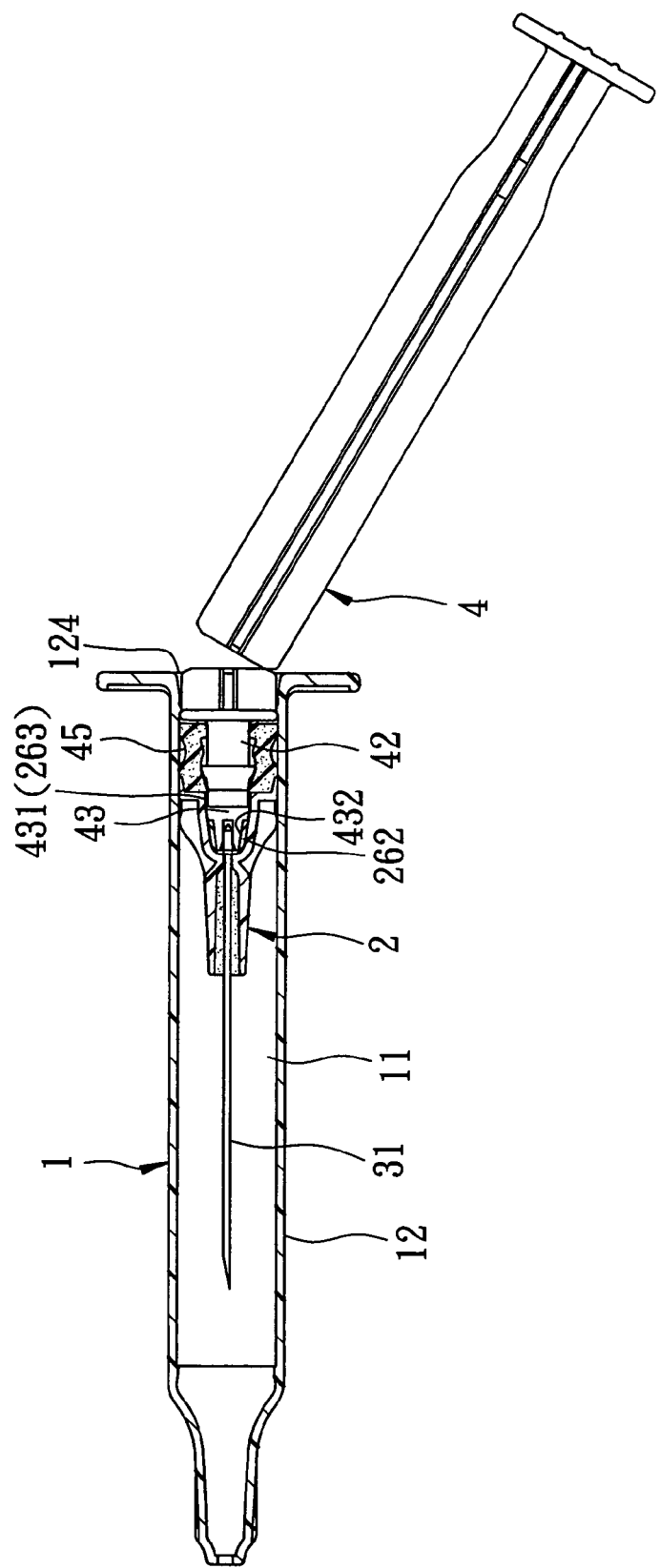
FIG. 6 is a sectional view of the first preferred embodiment in a disposal state.

Thereafter, continued movement of the engaging head 43 towards the ceiling wall 24, against the first frictional force, i.e. the frictional retention of the protrusion 28 in the annular recess 14, forces the fins 272 and the surrounding sealing flange 251 to move into the first and second friction diminishing regions 1271, 1272, respectively, until the surrounding flange surface 253 abuts against the shoulder abutment 13. Subsequent turning of the plunger 4 by the user to turn the needle seat 2 relative to the barrel 1 further diminish the friction therebetween to facilitate a subsequent pulling action of the plunger 4 whereby the needle seat 2 is brought towards the rear open end 124 by virtue of the retention of the rearwardly facing shoulder wall 431 by the radially yieldable catches 263, thereby retracting the needle cannula 31 into the passage 11, as shown in FIG. 6. Finally, the plunger 4 can be broken at a weakened part for convenient disposal of the syringe.

Figure 7:
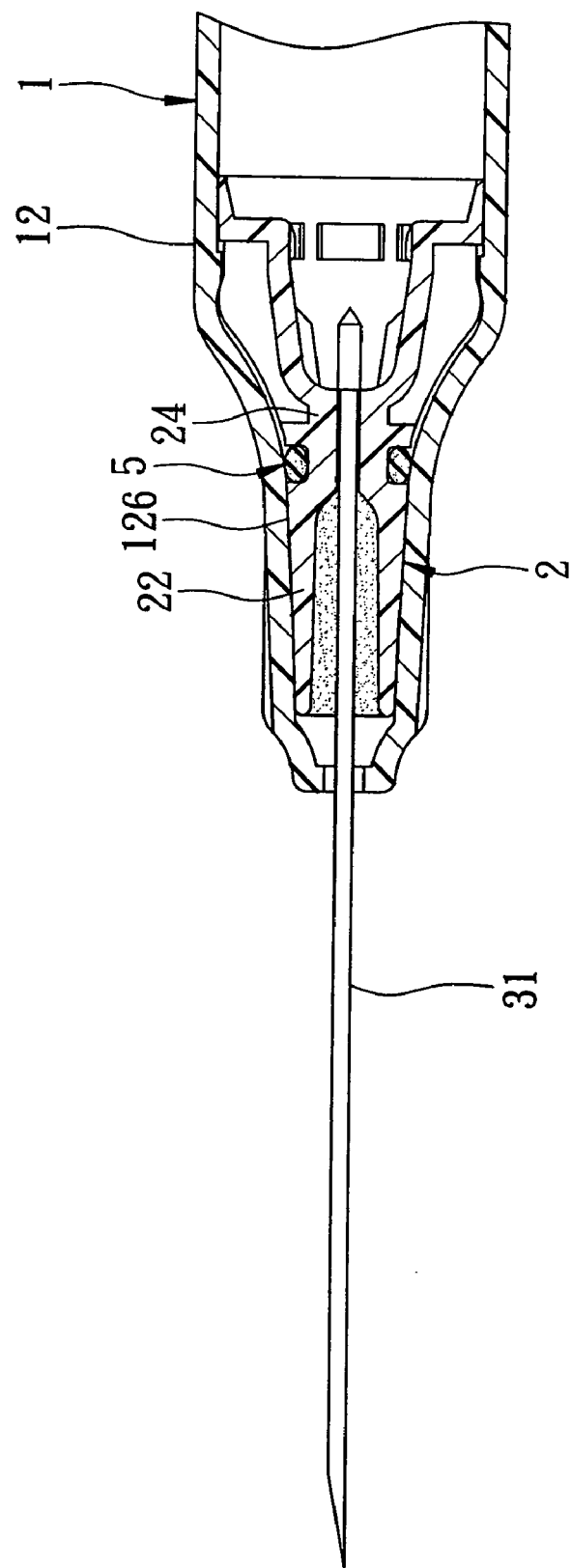
FIG. 7 is a fragmentary sectional view of the second preferred embodiment of a disposable syringe according to this invention.

FIG. 7 shows the second preferred embodiment of a disposable syringe according to this invention. In addition to the components of the first preferred embodiment described above, the disposable syringe of this embodiment further comprises an O-ring 5 which is sleeved tightly on the front engaging portion 22 of the needle seat 2, and which surrounds the axis (X) so as to enhance fluid-tightness of the engagement between the front surface segment 126 and the front engaging portion 22.

Figure 8:
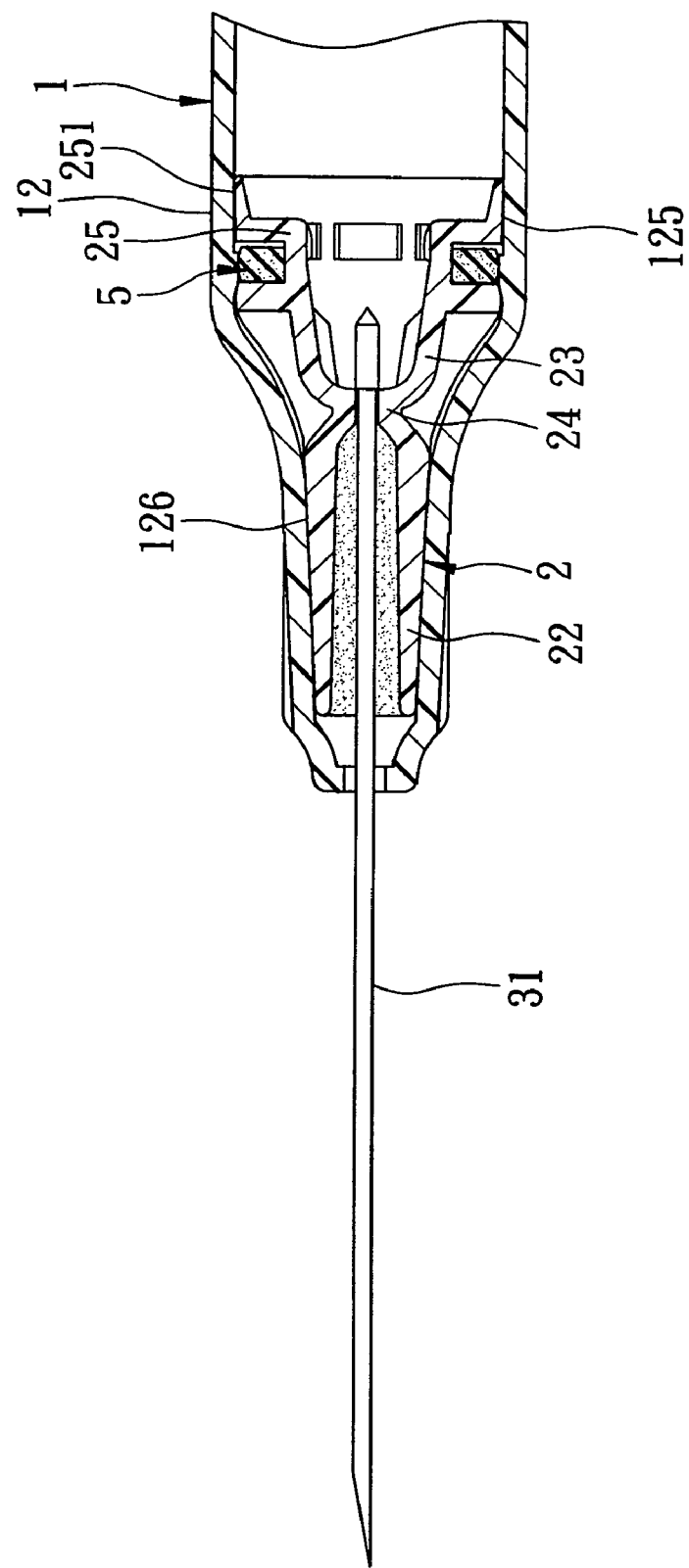
FIG. 8 is a fragmentary sectional view of the third preferred embodiment of a disposable syringe according to this invention.

In the third preferred embodiment of a disposable syringe shown in FIG. 8, an O-ring 5 is disposed on the rear engaging portion 25 so as to enhance fluid-tightness of the engagement between the rear surface segment 125 and the surrounding sealing flange 251.

Figure 9:
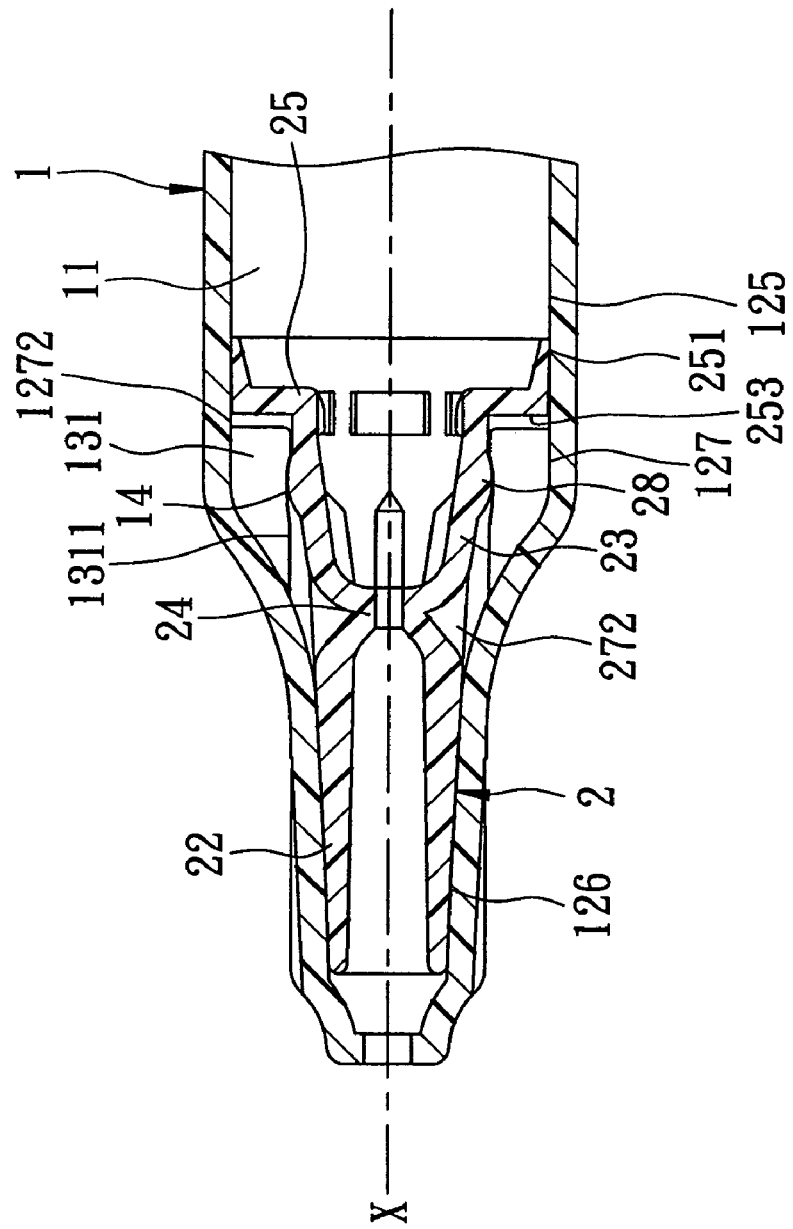
FIG. 9 is a fragmentary sectional view of the fourth preferred embodiment of a disposable syringe according to this invention, showing a needle seat retained in a barrel.

Referring to FIG. 9, the fourth preferred embodiment of a disposable syringe according to this invention is similar to the first preferred embodiment in construction. The differences reside in that the intermediate surface segment 127 has a plurality of fins 131 which are angularly displaced from one another about the axis (X) and which extend rearwardly to be spaced apart from the surrounding sealing flange 251 by the second friction diminishing region 1272. In addition, each of the fins 131 extends radially and inwardly to terminate at a distal end 1311. The distal ends 1311 of the fins 131 are configured such that a contour constituted by the distal ends 1311 about the axis (X) serves as the annular recess 14. Moreover, the retaining portion 23 is formed with an annular protrusion 28 to be retained in the recess 14 by virtue of the first frictional force. Furthermore, a plurality of fins 272 are formed on the ceiling wall 24, and are angularly displaced from one another.

Figure 10:
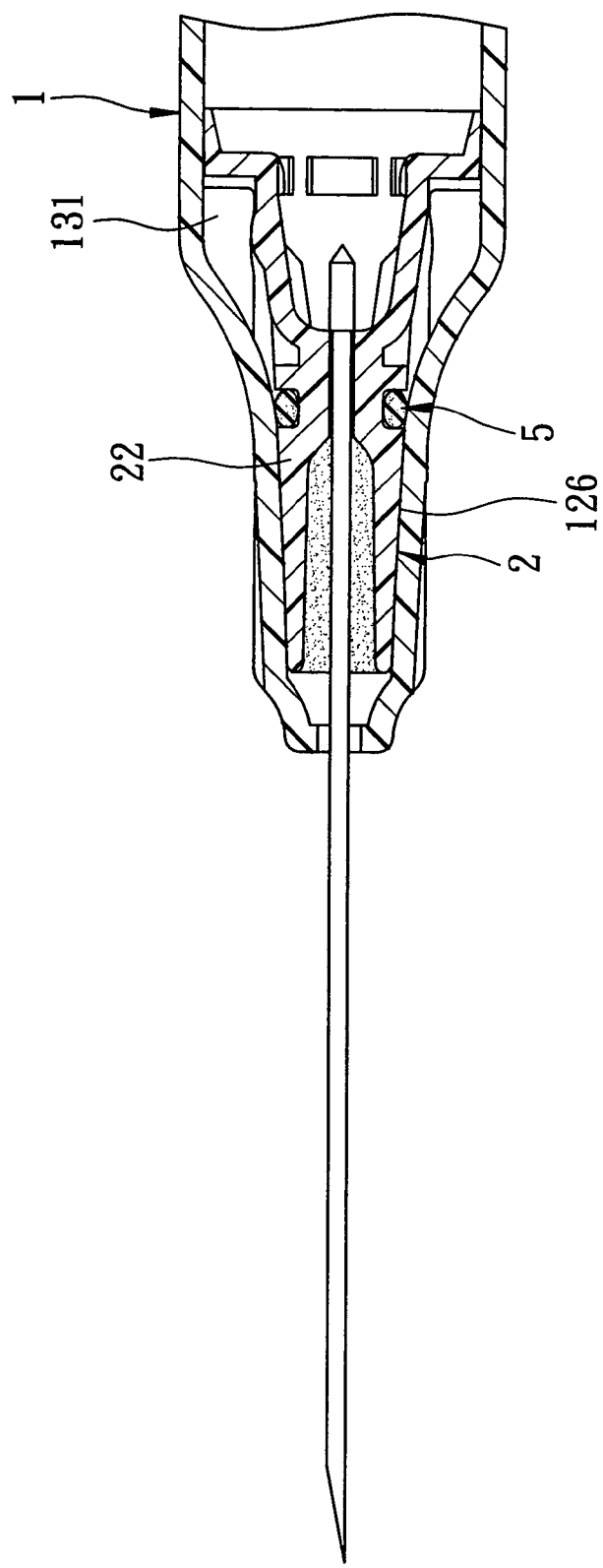
FIG. 10 is a fragmentary sectional view of the fifth preferred embodiment of a disposable syringe according to this invention, showing a needle seat retained in a barrel.

FIG. 10 shows the fifth preferred embodiment of a disposable syringe according to this invention, which is substantially similar to the fourth preferred embodiment. In this embodiment, an O-ring 5 is further sleeved tightly on the front engaging portion 22 of the needle seat 2, and is disposed to surround the axis (X) so as to enhance the fluid-tightness of the engagement between the front surface segment 126 and the front engaging portion 22.

Figure 11:
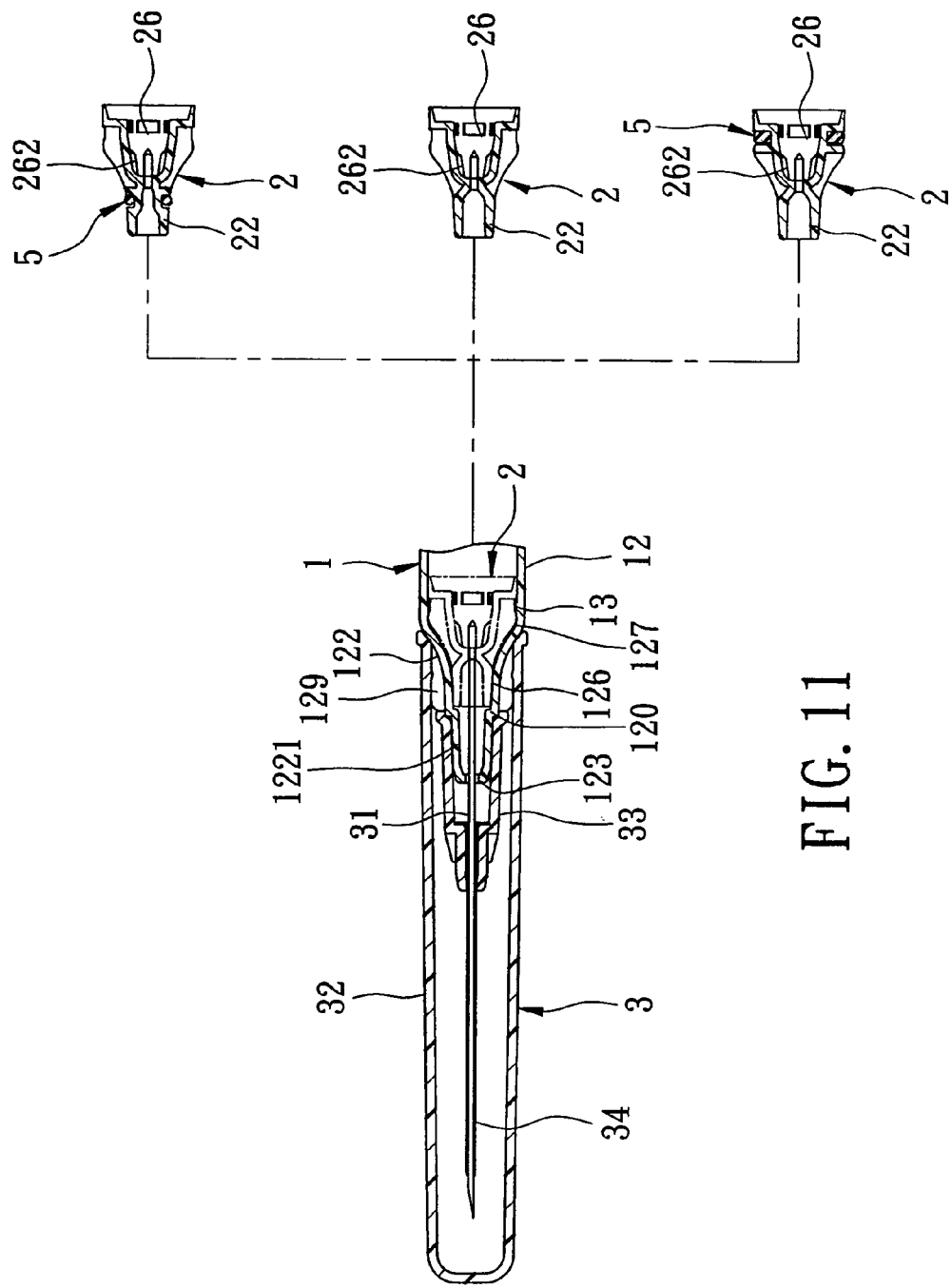
FIG. 11 is a fragmentary exploded sectional view of the sixth preferred embodiment of a disposable syringe according to this invention, showing three modified forms of needle seats for selective use with a barrel.
Figure 12:
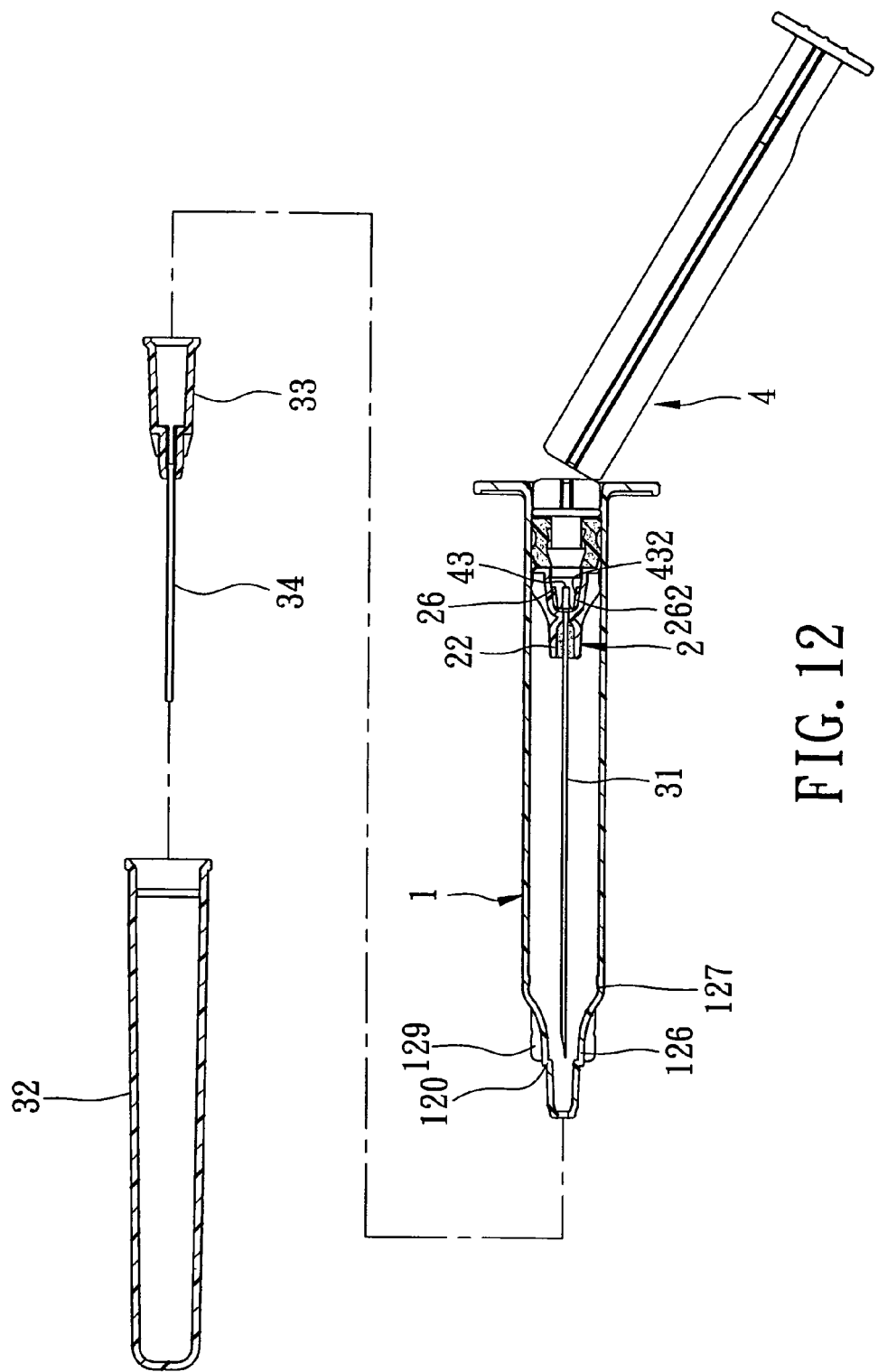
FIG. 12 is an exploded sectional view of the sixth preferred embodiment in a disposal state.

Referring to FIGS. 11 to 12, the sixth preferred embodiment of a disposable syringe is shown to include a selected one of the needle seats 2 of the above embodiments. In this embodiment, the outer wall surface 122 of the barrel 1 has an annular step portion 120 that faces forwardly, and that is distal from the front open end 123, and a surrounding front segment 1221 interposed between the front open end 123 and the annular step portion 120. The ribs 129 are formed rearwardly of the surrounding front segment 1221 so as to retainingly engage the tip protector 32. In addition, the disposable syringe further comprises a catheter hub 33 and a tubular catheter 34 for performing an intravenous catheter introducing process. Specifically, the catheter hub 33 includes a surrounding hub wall which has a sleeve portion that is sleeved on the surrounding front segment 1221 and that has a terminal edge abutting against the step portion 120, and a tip portion opposite to the sleeve portion along the axis (X). The tubular catheter 34 includes a proximate segment which is disposed in the tip portion and which extends along the axis (X), and a distal segment which extends from the proximate segment along the axis (X) to project outwardly of the tip portion. As such, after the tubular catheter 34 is introduced into a patient's vein by insertion of the needle cannula 31, the barrel 1 is separated from the catheter hub 33 so as to complete the intravenous catheter introducing process. The needle cannula 31 is then retracted into the barrel 1 in the same manner as described above, as shown in FIG. 12.

Figure 13:
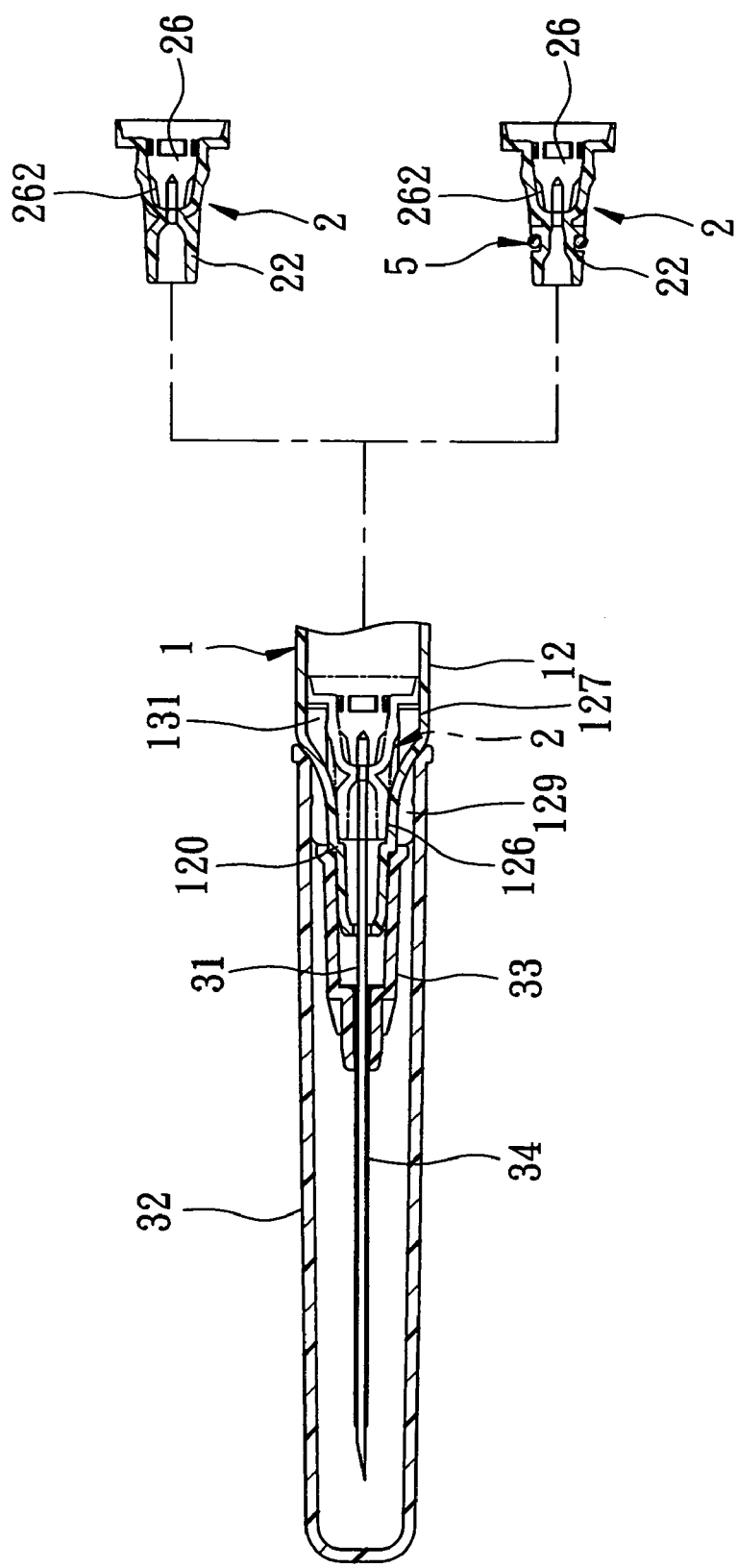
FIG. 13 is a fragmentary exploded sectional view of the seventh preferred embodiment of a disposable syringe according to this invention, showing two modified forms of needle seats for selective use with a barrel.
Figure 14:
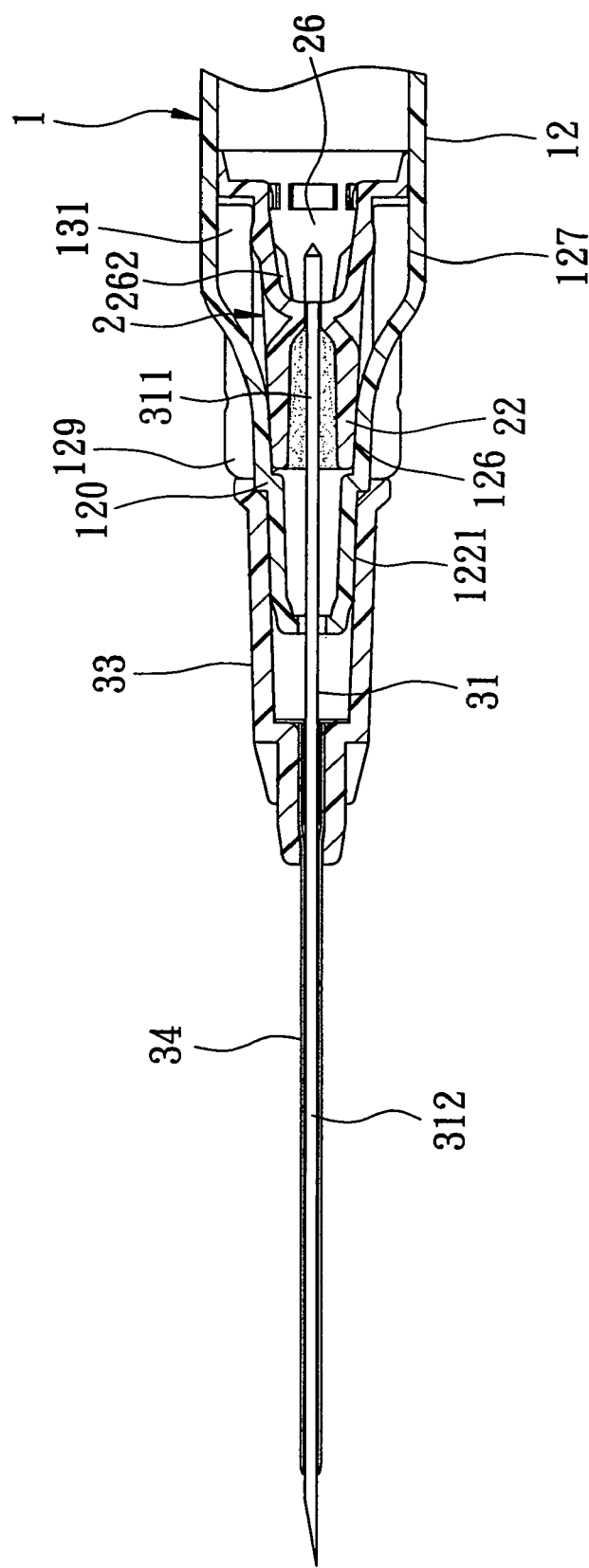
FIG. 14 is a fragmentary sectional view of the seventh preferred embodiment, showing a selected one of the needle seats retained in the barrel.

Referring to FIGS. 13 and 14, the seventh preferred embodiment of a disposable syringe is shown to be similar to the sixth preferred embodiment in construction and function, except that the barrel 1 and the needle seat 2 are the same as those of the fourth and fifth preferred embodiments shown in FIGS. 9 and 10. Furthermore, the front engaging portion 22 of the needle seat 2 is filled with an adhesive to affix a secured segment 311 of the needle cannula 31 to the front engaging portion 22.

Figure 15:
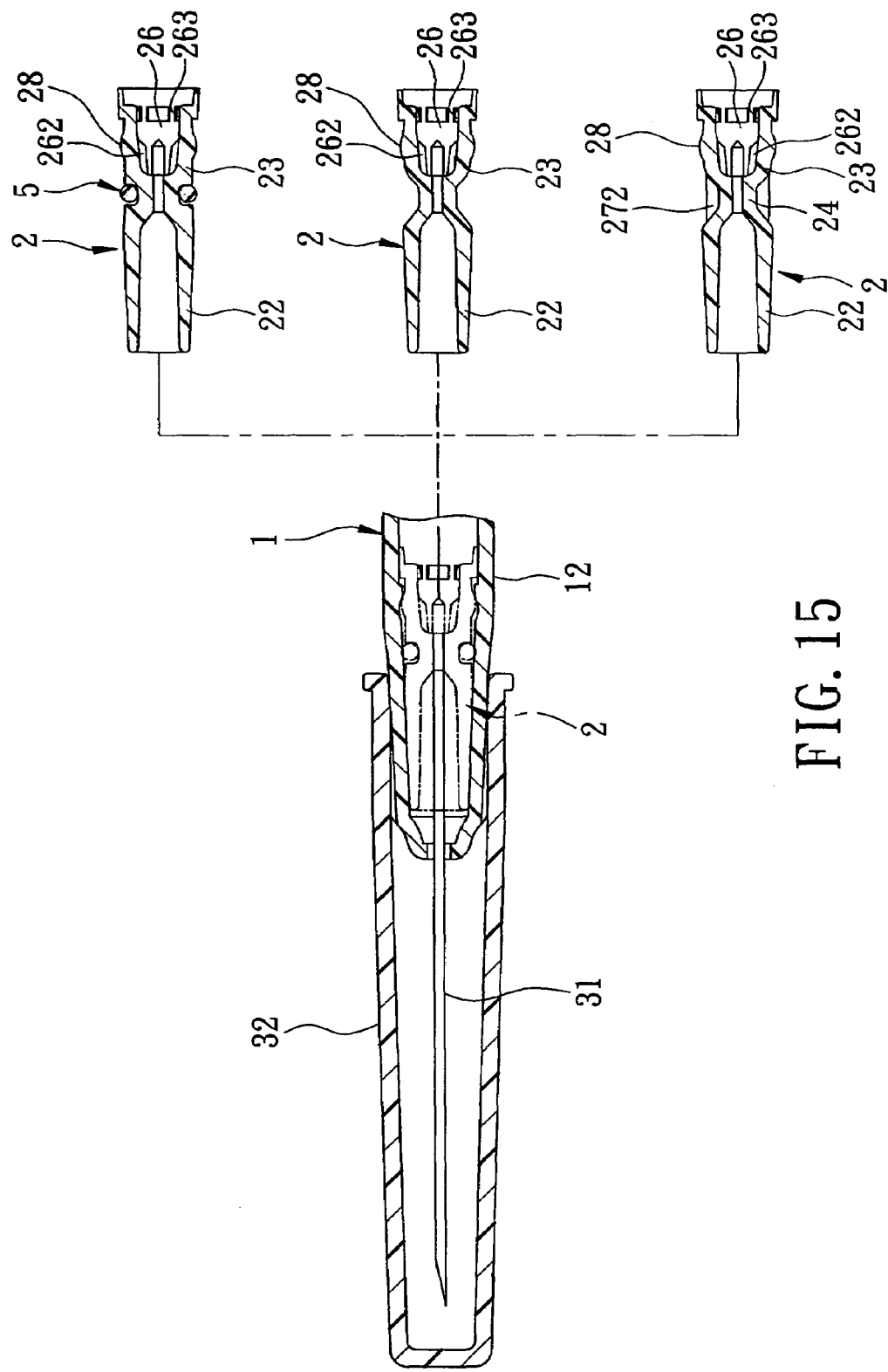
FIG. 15 is a fragmentary exploded sectional view of the eighth preferred embodiment of a disposable syringe according to this invention, showing three modified forms of needle seats for selective use with a barrel.
Figure 16:
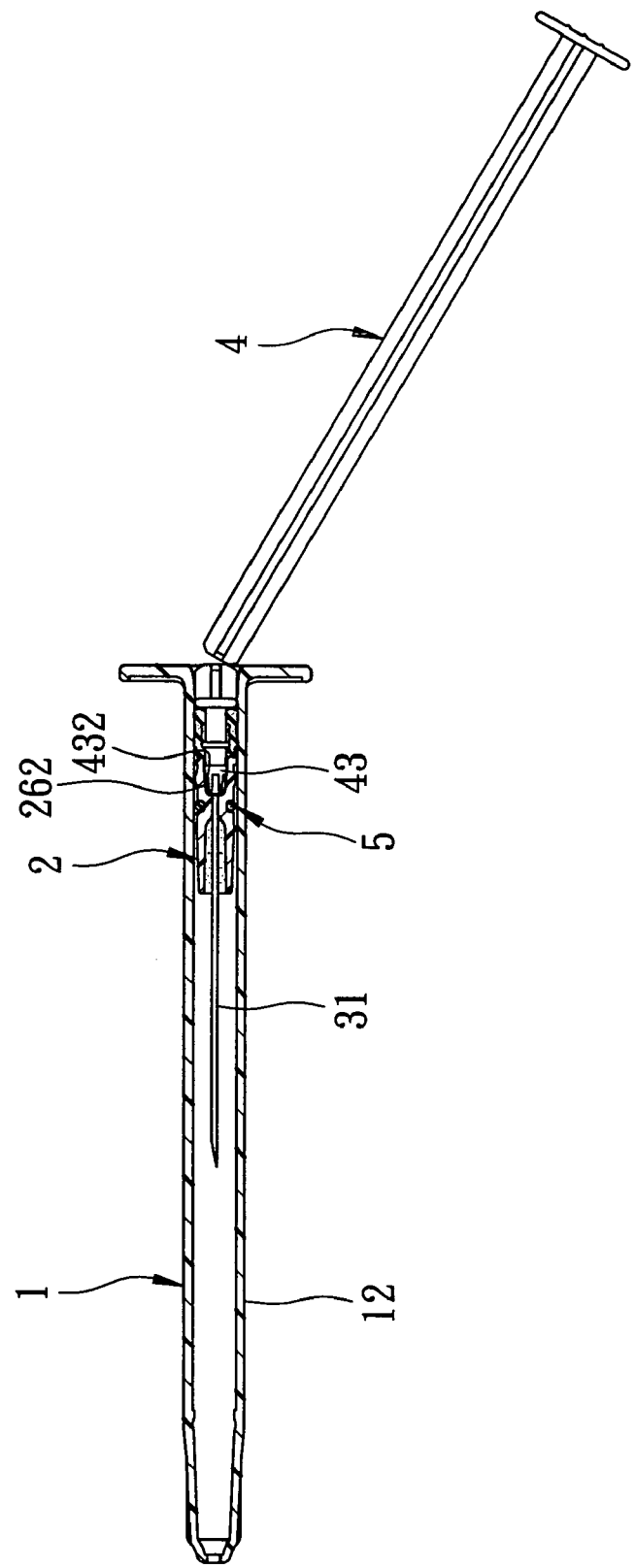
FIG. 16 is a fragmentary sectional view of the eighth preferred embodiment in a disposal state, showing a selected one of the needle seats retained in the barrel.

Referring to FIGS. 15 and 16, the disposable syringe of the eighth preferred embodiment is adapted for injecting medication of an extremely small volume, such as 1 ml. That is, the barrel 1 and the plunger 4 have relatively smaller diameters. The needle seat 2 may have an O-ring 5 or fins 272 disposed on the ceiling wall 24.

Figure 17:
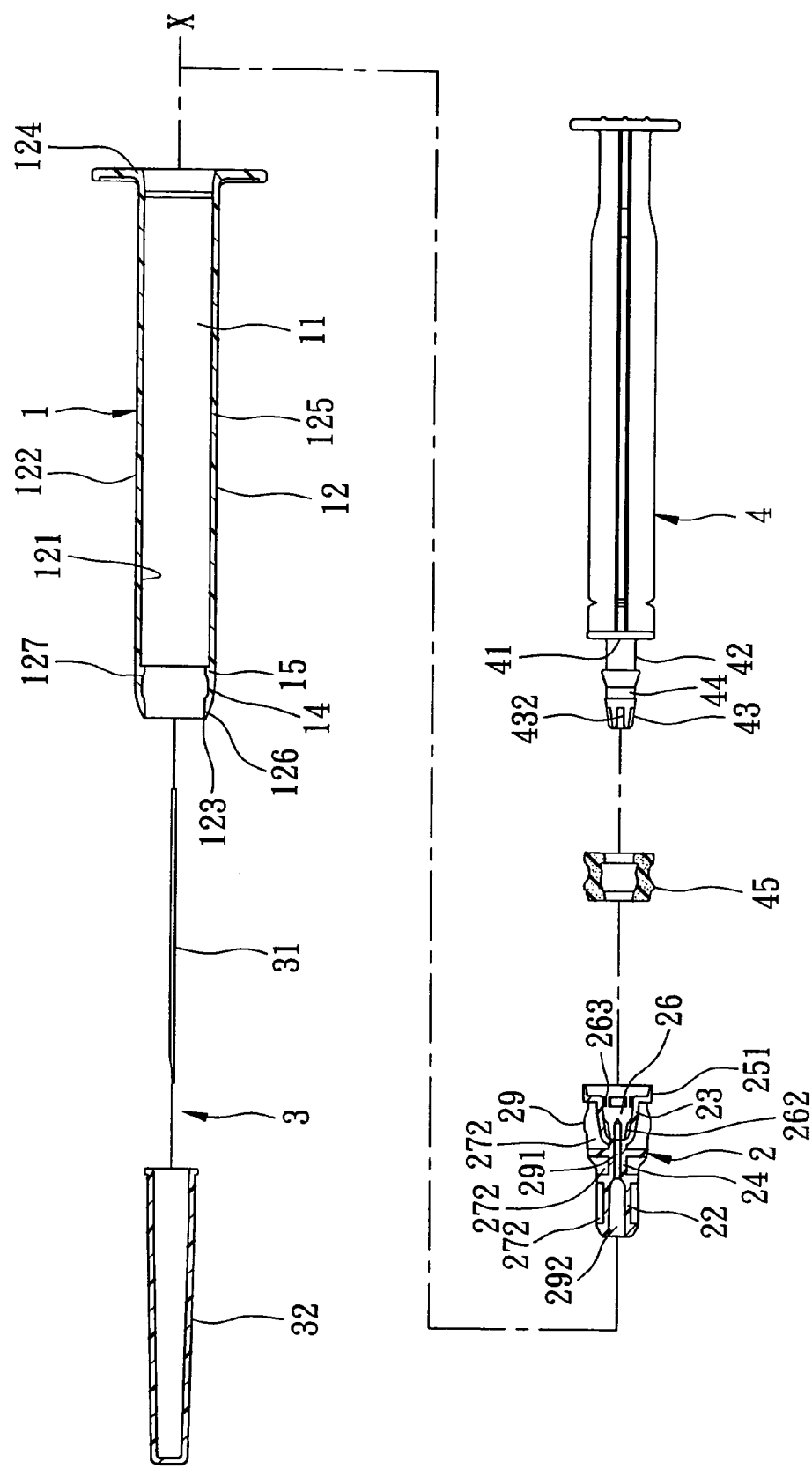
FIG. 17 is an exploded sectional view of the ninth preferred embodiment of a disposable syringe according to this invention.
Figure 18:
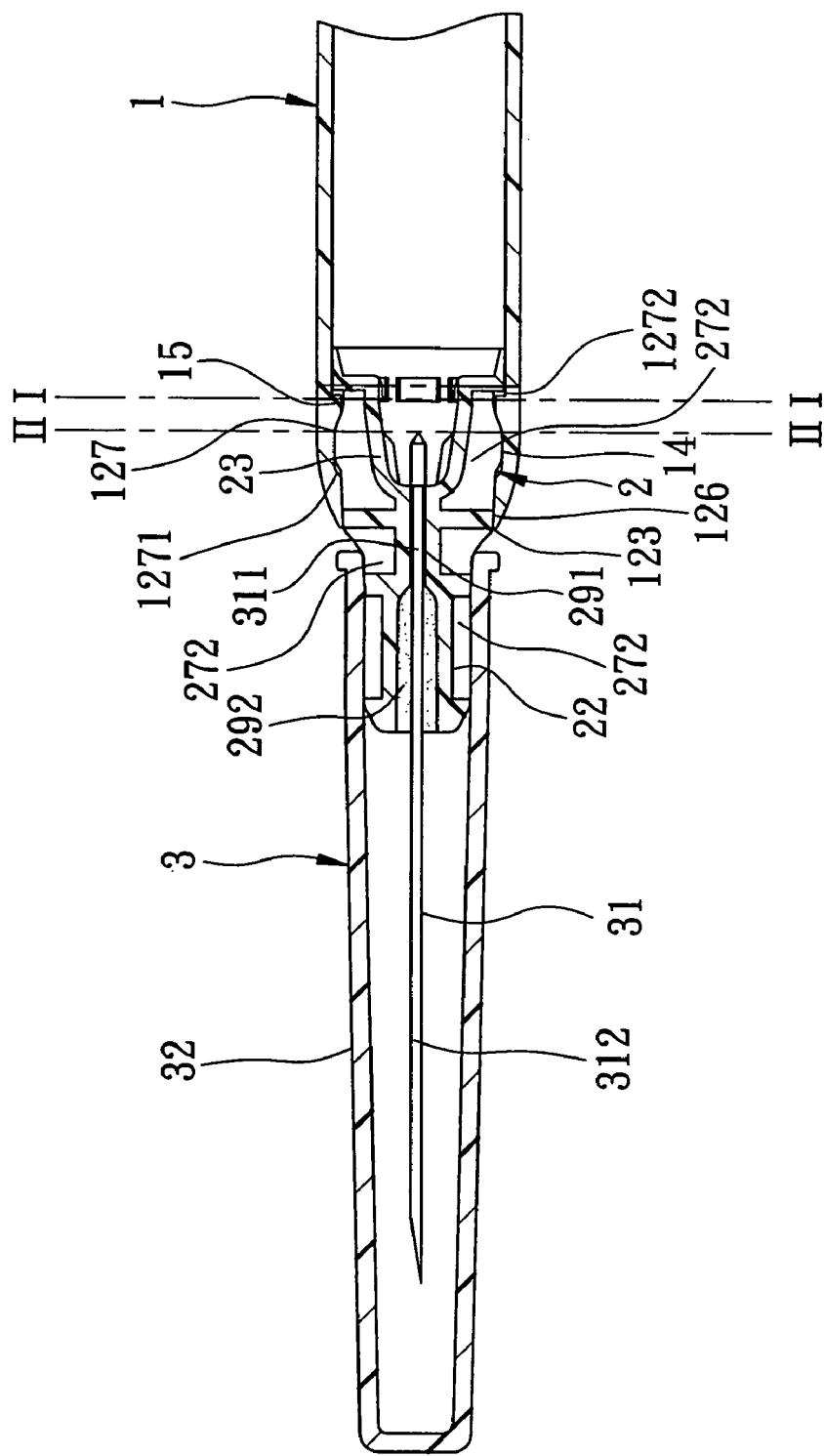
FIG. 18 is a fragmentary sectional view of the ninth preferred embodiment, showing a needle seat retained in a barrel.
Figure 19:
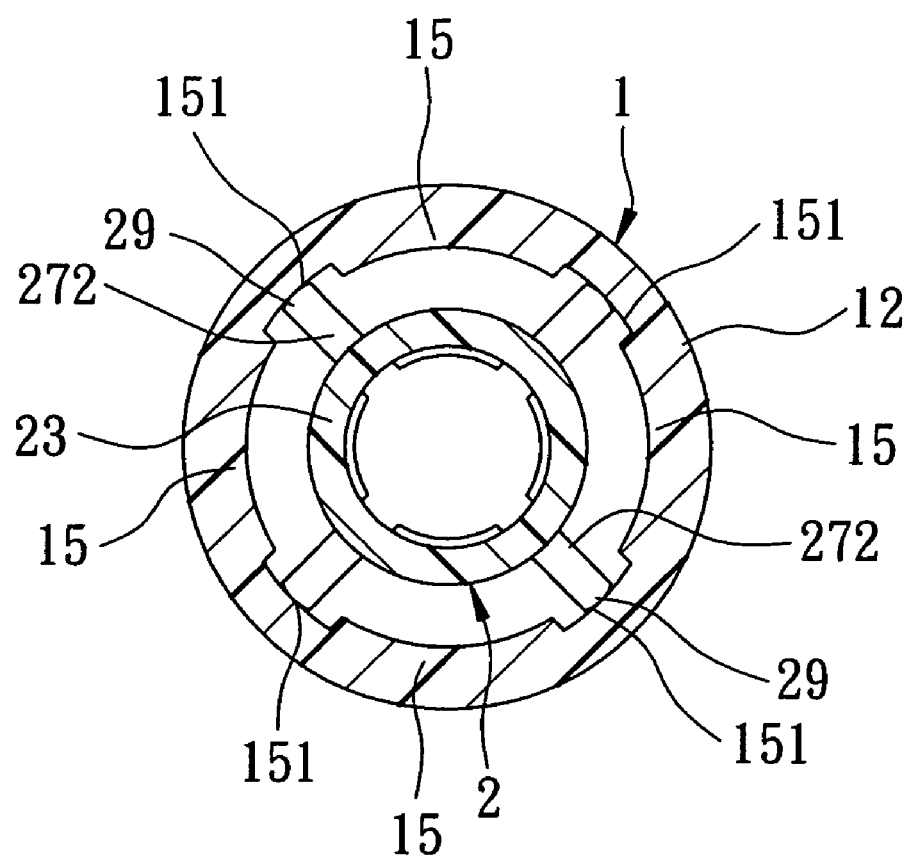
FIG. 19 is a partly cross-sectional view of a barrier portion taken along lines I-I of FIG. 18.
Figure 20:
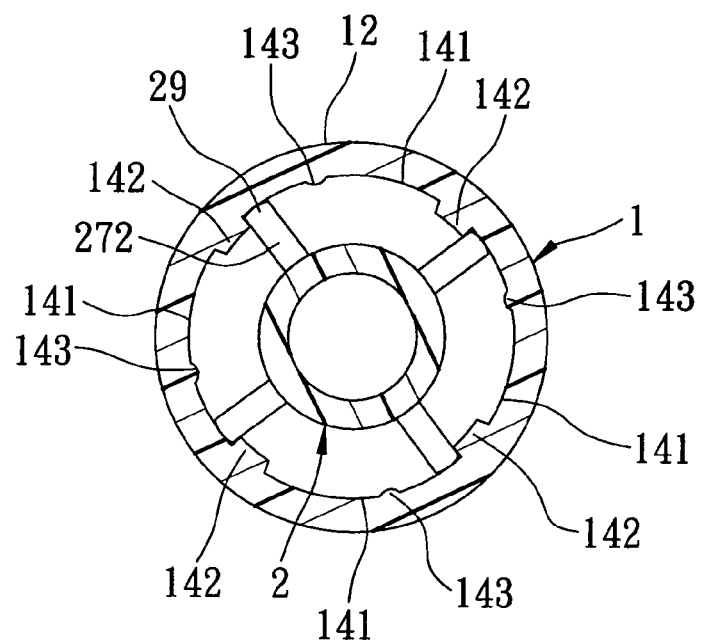
FIG. 20 is a partly cross-sectional view of a retaining portion taken along lines II-II of FIG. 18.

Referring to FIGS. 17 and 18, the ninth preferred embodiment of a disposable syringe according to this invention is shown to be similar to the first preferred embodiment in construction. The differences therebetween are as follows. The front engaging portion 22 of the needle seat 2 has a seat segment which is configured to extend outwardly of the barrel 1 from the front open end 123 when the needle seat 2 is in the position of use. With reference to FIG. 19, the intermediate surface segment 127 has a plurality of barriers 15 which are angularly displaced from one another about the axis (X) so as to define a recessed access 151 between two adjacent ones of the barriers 15. With reference to FIG. 20, the retaining region 14 has a plurality of recesses 141 which are angularly displaced from one another about the axis (X) and which are spaced apart from one another by protrusions 142, and a plurality of bumps 143 respectively extending from the recesses 141 inwardly and radially.

The retaining portion 23 of the needle seat 2 has a plurality of partitions 272 in the form of fins 272 which are angularly displaced from one another about the axis (X), and a plurality of blocking segments 29 which respectively extend from the partitions 272 radially and outwardly. As mentioned above, when the needle seat 2 is brought to be inserted into the passage 11 from the rear open end 124 during assembly, and immediately after each of the partitions 272 is brought to pass the corresponding recessed access 151 between two adjacent ones of the barriers 15, as shown in FIG. 19, each of the partitions 272 is turned a predetermined angle in one of clockwise and counterclockwise directions such that each of the blocking segments 29 is received in and is engaged with a respective one of the recesses 141 by virtue of the first frictional force, as shown in FIG. 20, while being prevented by the corresponding barrier 15 from axial movement relative to the second diminishing region 1272, thereby placing the needle seat 2 firmly in the position of use.

Figure 21:
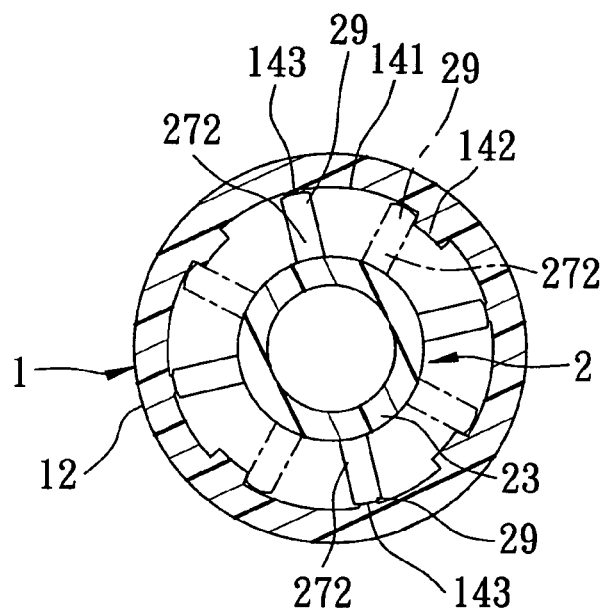
FIG. 21 is a view similar to FIG. 20, but showing how a needle seat is turned relative to the retaining member to another angular position.
Figure 22:
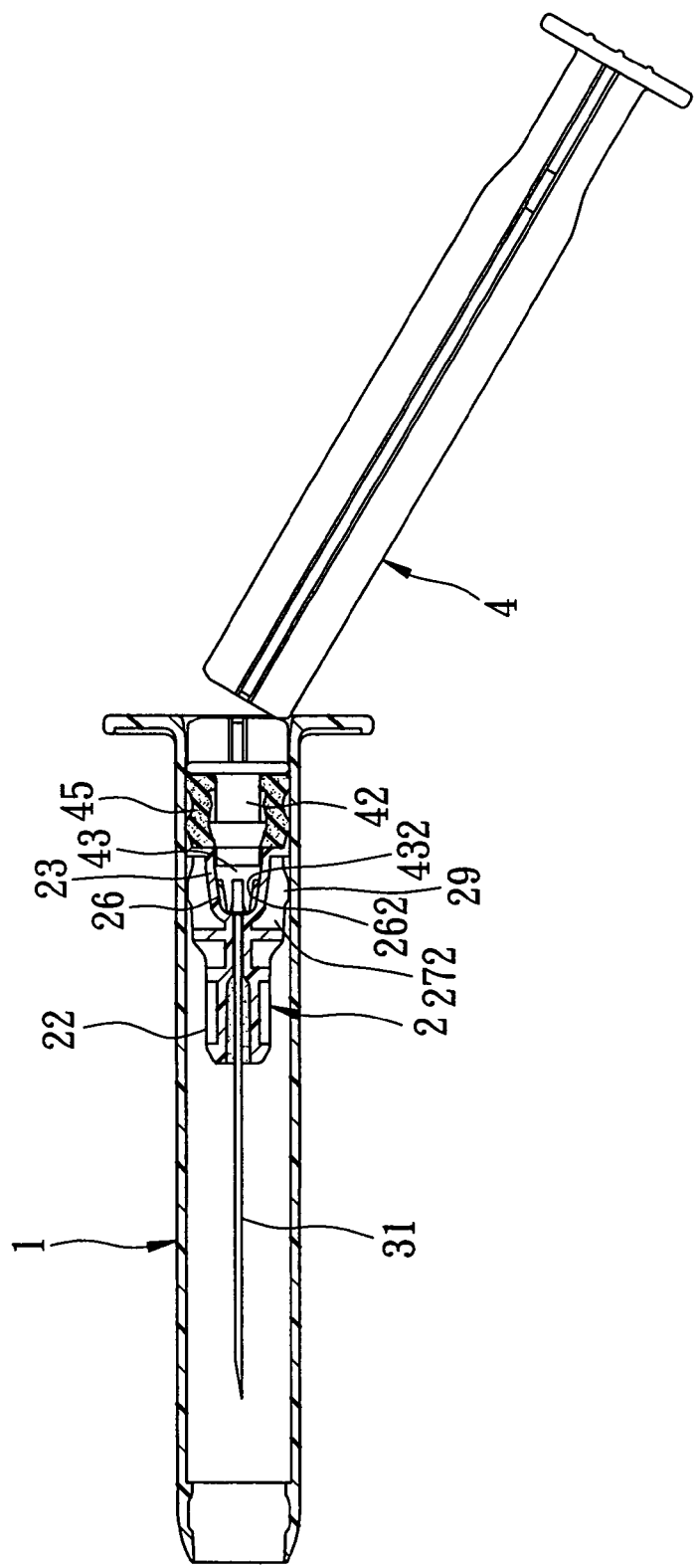
FIG. 22 is a sectional view of the ninth preferred embodiment in a disposal state.

Moreover, when the plunger 4 is placed in the disposal position and the needle seat 2 is retained onto the plunger 4, the user can rotate the needle seat 2 so that the partitions 272 are turned the predetermined angle in a corresponding one of the counterclockwise and clockwise directions, as indicated by dotted lines in FIG. 21 so that the blocking segments 29 slip over the bumps 143, respectively (as indicated by solid lines in FIG. 21). Thus, the user can be aware of the approaching of the blocking segments 29 to a position where the blocking segments 29 are unrestrained by the barriers 15 and are permitted to perform the axial movement. Therefore, the needle seat 2 is allowed to be pulled rearwardly so as to retract the needle cannula 31 into the passage 11, as shown in FIG. 22.

Furthermore, in addition to having the partitions 272 formed on the retaining portion 23, the needle seat 2 has a plurality of fins 272 formed on the ceiling wall 24 and on the seat segment of the front engaging portion 22. The tip protector 32 is disposed to sleeve on and is frictionally retained onto the seat segment of the front engaging portion 22 for shielding the sharp segment 312 of the needle cannula 31.

Figure 23:
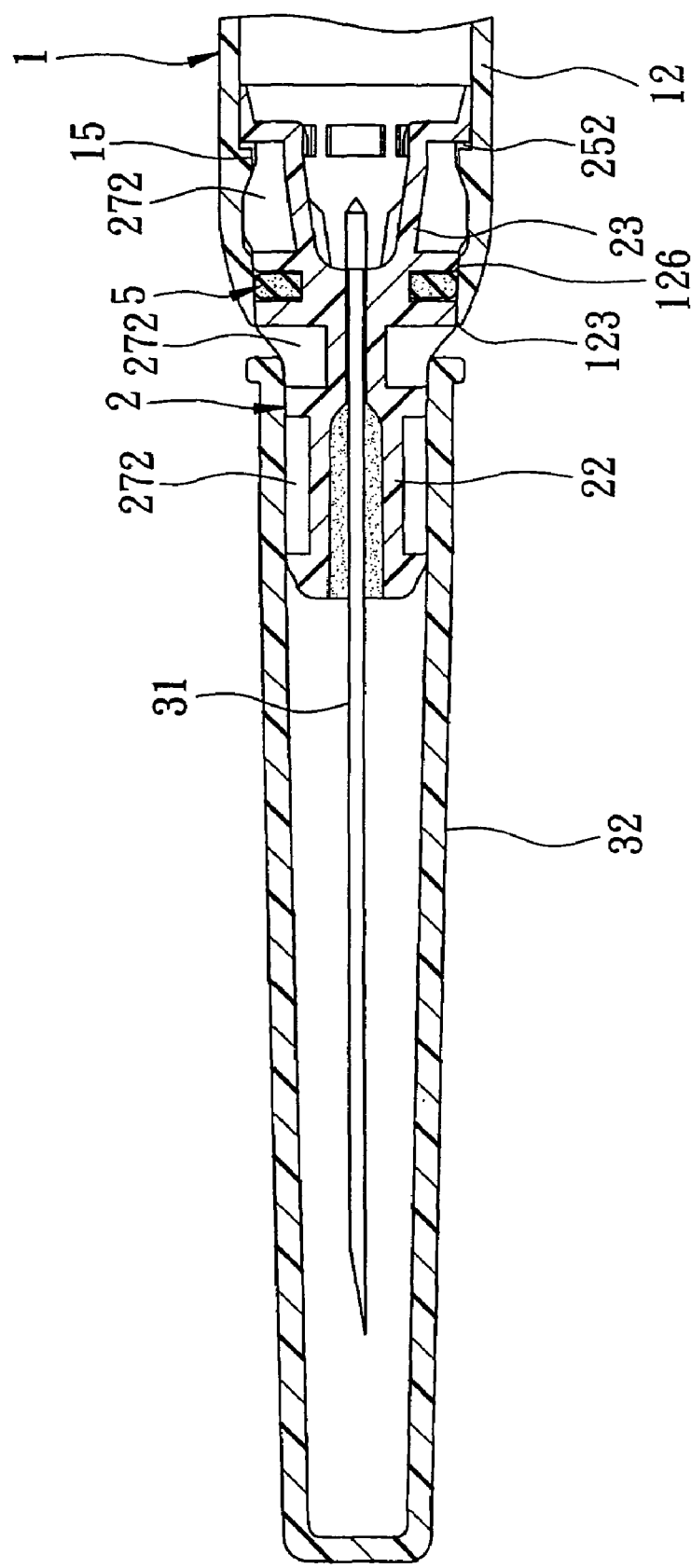
FIG. 23 is a fragmentary sectional view of the tenth preferred embodiment of a disposable syringe according to this invention.

Referring to FIG. 23, the tenth preferred embodiment of a disposable syringe according to this invention is similar to the ninth preferred embodiment, and further comprises an O-ring 5 which is disposed on the front engaging portion 22 of the needle seat 2 so as to enhance fluid-tightness of the engagement between the front engaging portion 22 and the front surface segment 126 of the barrel 1.

Figure 24:
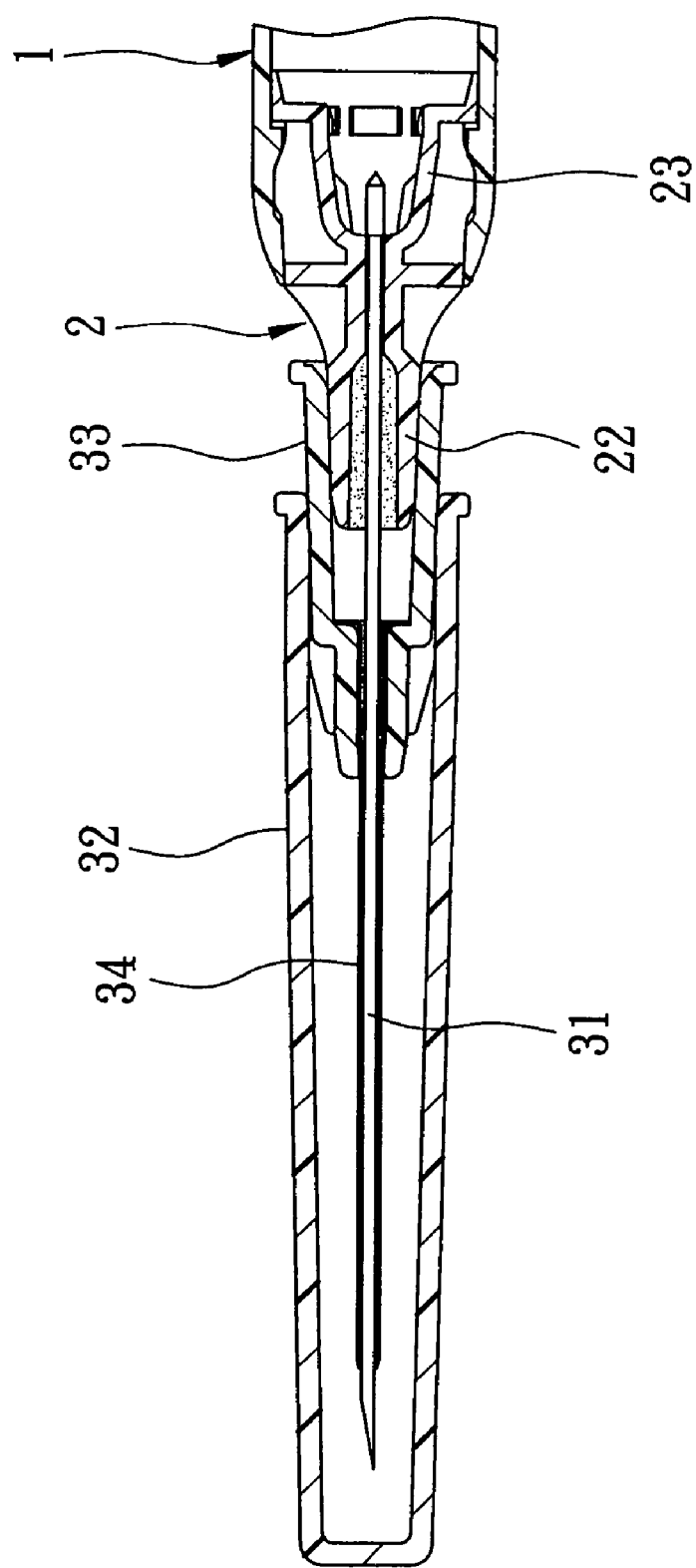
FIG. 24 is a fragmentary sectional view of the eleventh preferred embodiment of a disposable syringe according to this invention.
Figure 25:
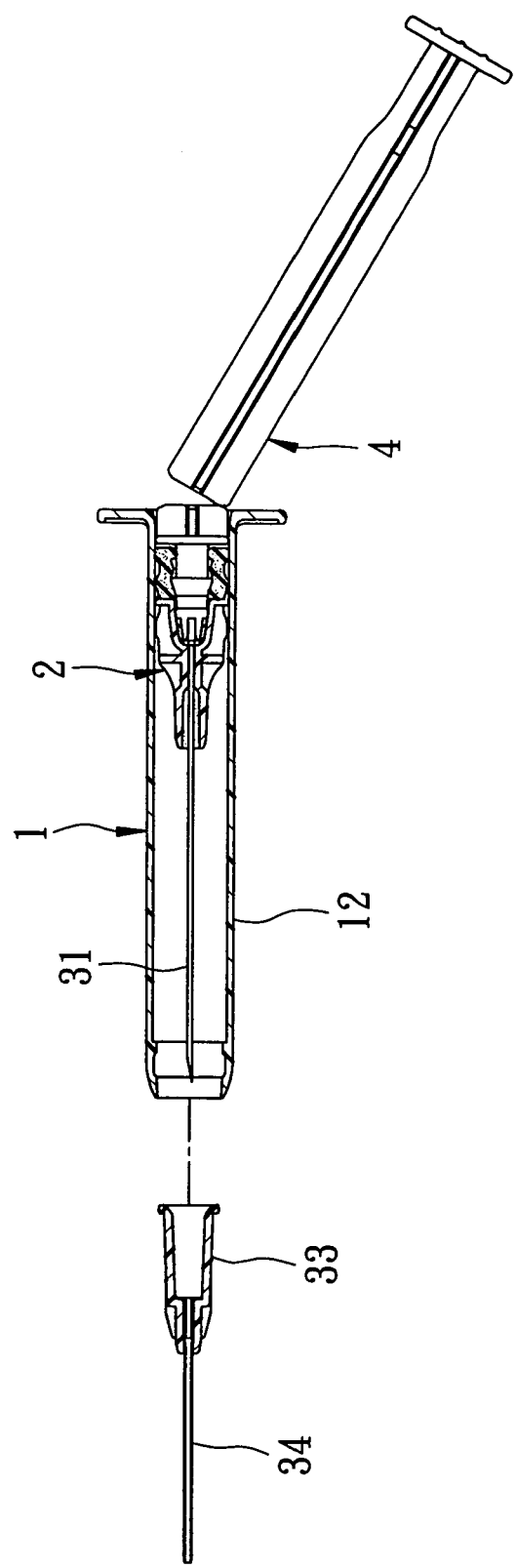
FIG. 25 is a sectional view of the eleventh preferred embodiment in a disposal state.

Referring to FIGS. 24 and 25, in the eleventh preferred embodiment of a disposable syringe according to this invention, a catheter hub 33 and a tubular catheter 34 are further provided for performing an intravenous catheter introducing process. The catheter hub 33 includes a surrounding hub wall which has a sleeve portion that is sleeved on the seat segment of the front engaging portion 22, and a tip portion opposite to the sleeve portion along the axis (X). The tubular catheter 34 includes a proximate segment which is disposed in the tip portion and which extends along the axis (X), and a distal segment which extends from the proximate segment along the axis (X) and outwardly of the tip portion. Moreover, since the sleeve portion of the catheter hub 33 is sleeved on the seat segment of the front engaging portion 22, there is no need to form fins on the seat segment.

Figure 26:
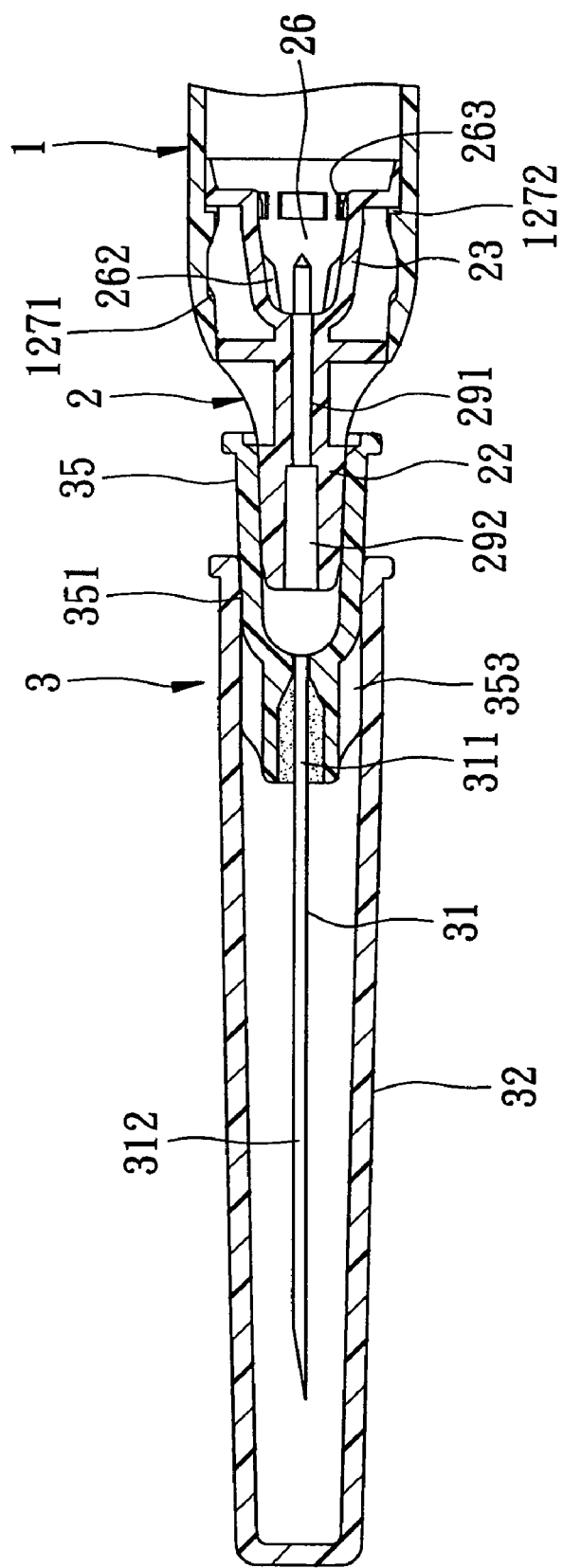
FIG. 26 is a fragmentary sectional view of the twelfth preferred embodiment of a disposable syringe according to this invention.
Figure 27:
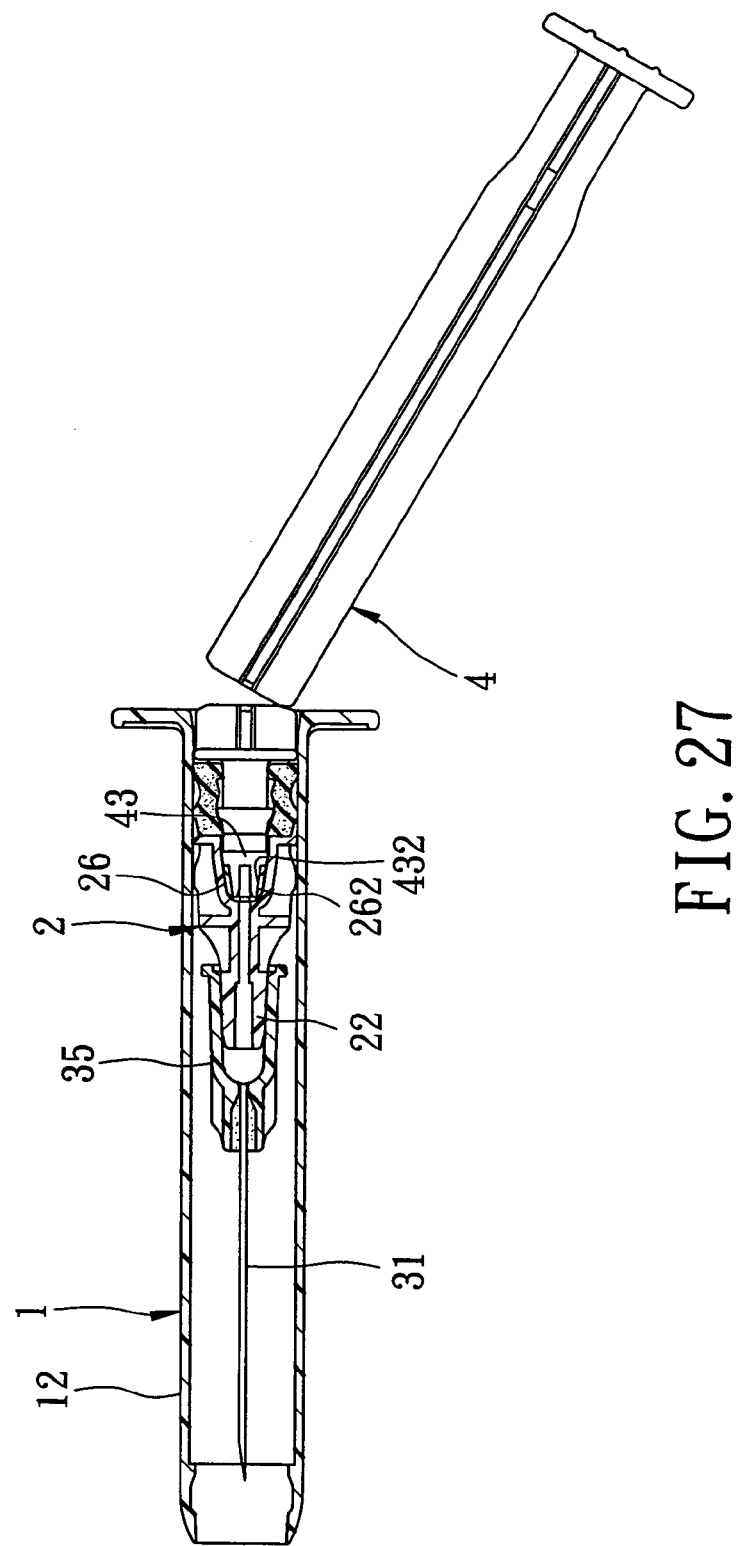
FIG. 27 is a sectional view of the twelfth preferred embodiment in a disposal state.

Referring to FIGS. 26 and 27, the twelfth preferred embodiment of a disposable syringe according to this invention is shown to be similar to the ninth preferred embodiment. In this embodiment, the needle seat 2 further includes a hub segment 35 which is configured to fix the secured segment 311 of the needle cannula 31 along the axis (X), and which is sleeved on the seat segment of the front engaging portion 22 to establish fluid communication between the needle cannula 31 and the axial hole 291 through the filling hole 292 which is free from adhesive. The hub segment 35 has a rib portion 353 formed on an outer surface 351 thereof so as to retain the tip protector 32 for shielding the sharp segment 312 of the needle cannula 31.

Figure 28:
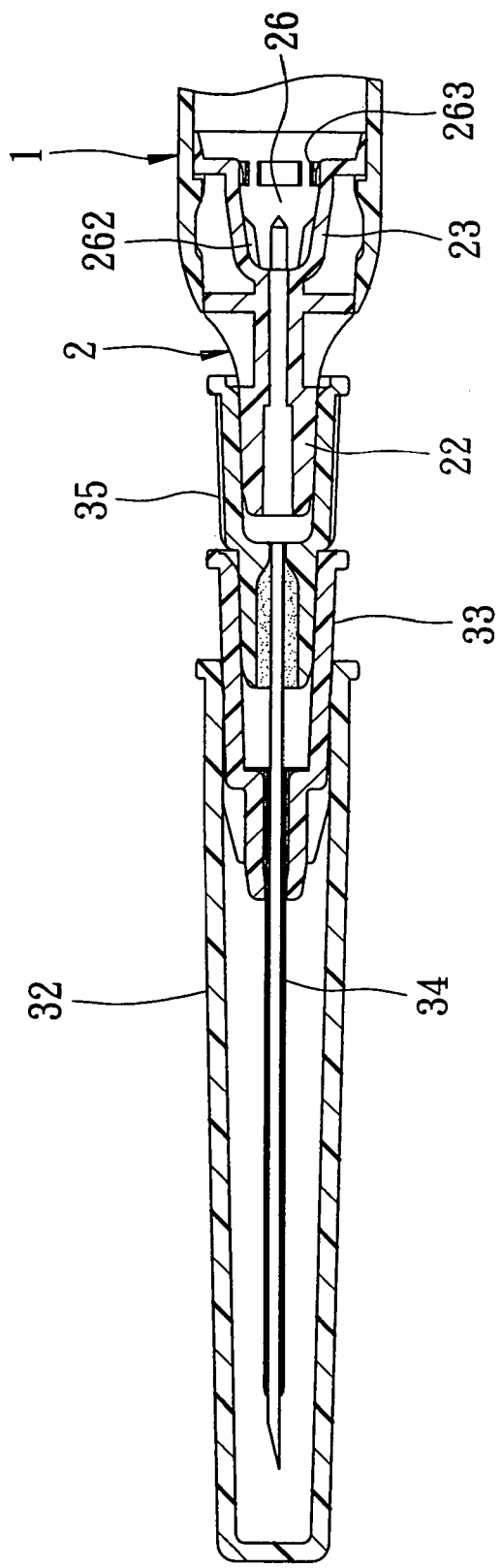
FIG. 28 is a fragmentary sectional view of the thirteenth preferred embodiment of a disposable syringe according to this invention.
Figure 29:
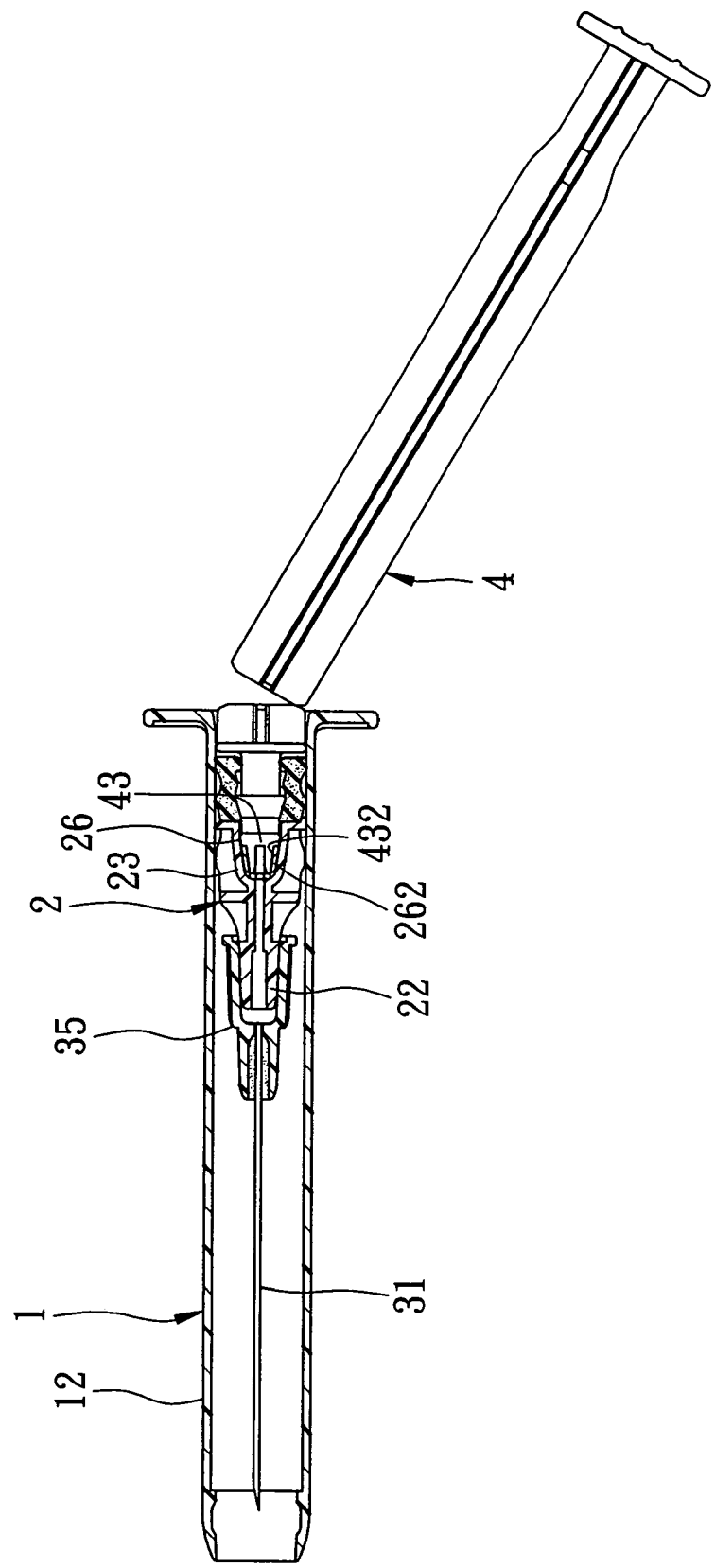
FIG. 29 is a sectional view of the thirteenth preferred embodiment in a disposal state.

Referring to FIGS. 28 and 29, the thirteenth preferred embodiment of a disposable syringe according to this invention is shown to be similar to the twelfth preferred embodiment in construction, and further comprises a catheter hub 33 and a tubular catheter 34 for performing an intravenous catheter introducing process. That is, the catheter hub 33 includes a surrounding hub wall which has a sleeve portion sleeved on the hub segment 35, and a tip portion opposite to the sleeve portion along the axis (X). The tubular catheter 34 includes a proximate segment which is disposed in the tip portion and which extends along the axis (X), and a distal segment which extends from the proximate segment along the axis (X) and outwardly of the tip portion. The tip protector 32 is sleeved retainingly on the surrounding hub wall of the catheter hub 33.

Figure 30:
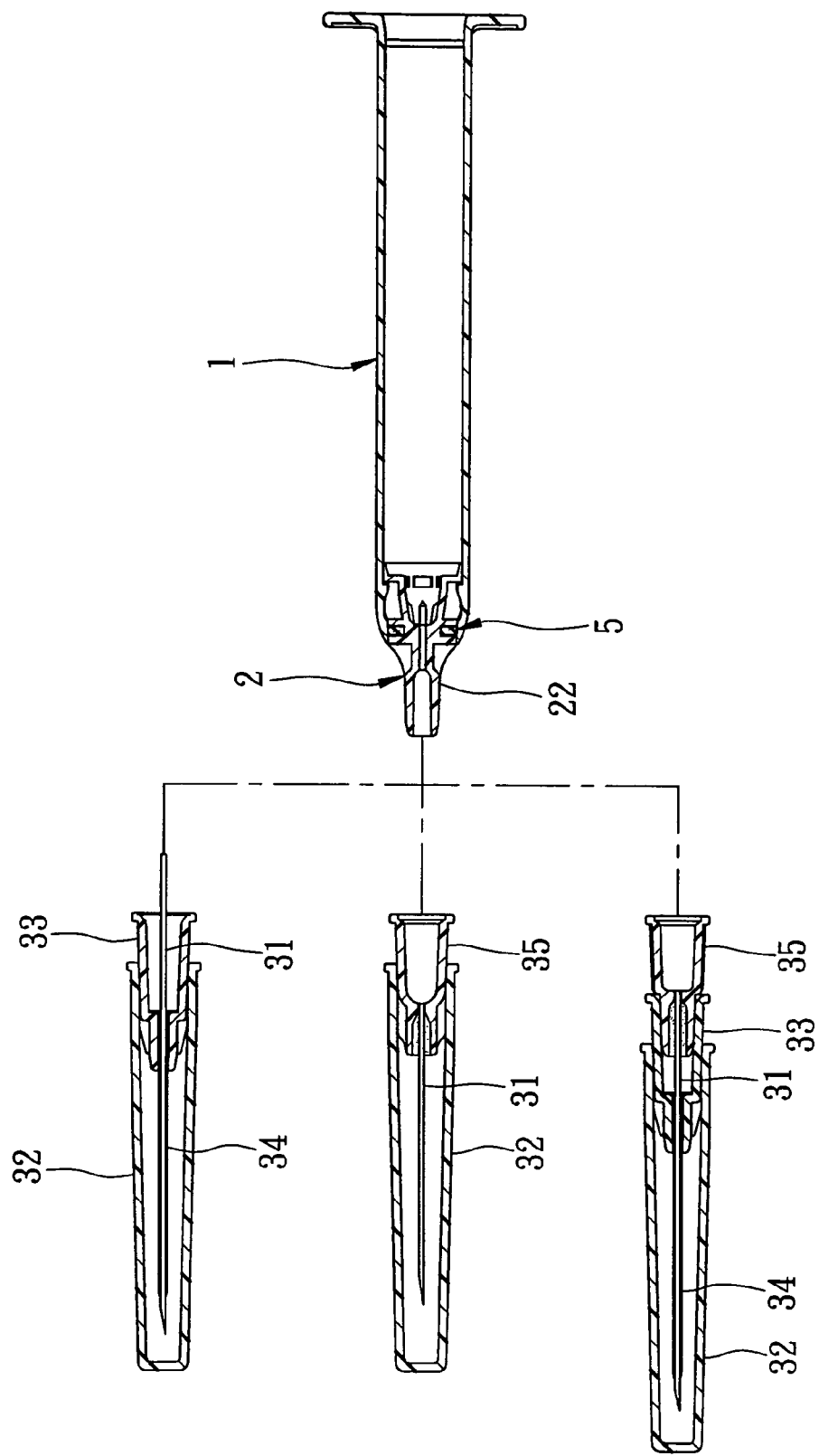
FIG. 30 is an exploded sectional view of the fourteenth preferred embodiment of a disposable syringe according to this invention, showing three modified forms of needle assembly for selective use with a barrel.

Referring to FIG. 30, in the fourteenth preferred embodiment of a disposable syringe according to this invention, which has a construction similar to that of the eleventh preferred embodiment, an O-ring 5 is additionally disposed on the front engaging portion 22 of the needle seat 2. Moreover, any forms of the needle assembles 3, such as that including the catheter hub 33 and the tubular catheter 34, that including the hub segment 35, and that including the catheter hub 33, the tubular catheter 34 and the hub segment 35, can be provided for use with the needle seat 2 as required.

The advantages of the disposable syringe of this invention are as follows:

1. The retaining portion 23 and the surrounding sealing flange 251 are moved into the first and second friction diminishing regions 1271, 1272, respectively, when the plunger 4 is to be placed in the disposal position so as to diminish the friction between the needle seat 2 and the inner wall surface 121 of the barrel 1, thereby facilitating a subsequent pulling action of the plunger 4 for retracting the needle cannula 31 into the barrel 1. Moreover, by virtue of the splined engagement between the axially extending ribs 262 and the grooves 432, the needle seat 2 is rotated with the plunger 4 to thereby further diminish the friction between the needle seat 2 and the inner wall surface 121 of the barrel 1. Therefore, the retraction of the needle cannula 31 can be successful and steady.

2. The provision of angularly displaced fins 272 on the needle seat 2 helps prevent contraction and deformation of the needle seat 2 during plastic injection molding due to the cohesion property of the plastic material, thereby reducing failure in production.

3. Since the front engaging portion 22 and the surrounding sealing flange 251 of the needle seat 2 are in fluid-tight engagement with the front and rear surface segments 126, 125 of the barrel 1, the engagement being enhanced by the provision of O-rings 5 and by virtue of the first frictional force generated between the retaining portion 23 (the protrusion 28) and the retaining region 14 (the annular recess 14), the needle seat 2 can be firmly retained in the passage 11 of the barrel 1 with a fluid-tight engagement therebetween.

While the present invention has been described in connection with what is considered the most practical and preferred embodiments, it is understood that this invention is not limited to the disclosed embodiments but is intended to cover various arrangements included within the spirit and scope of the broadest interpretations and equivalent arrangements.

We claim:

1. A disposable syringe comprising:
   a barrel having a surrounding barrel wall which surrounds an axis in a longitudinal direction and which defines a passage therein that has front and rear open ends opposite to each other, said surrounding barrel wall having an inner wall surface which includes front and rear surface segments proximate to said front and rear open ends, respectively, and an intermediate surface segment disposed therebetween, said intermediate surface segment having a retaining region which is axially distal from said front surface segment, and first and second friction diminishing regions which are respectively interposed between said retaining region and said front surface segment, and between said retaining region and said rear surface segment;
   a needle cannula;
   a tubular needle seat configured to be insertable into said passage from said rear open end, and surrounding the axis, said needle seat including
      a front engaging portion which is configured to be in fluid-tight engagement with said front surface segment and which is disposed to fix said needle cannula along the axis,
      a retaining portion which is disposed rearwardly of said front engaging portion, and which is retained at said retaining region by virtue of a first frictional force when said needle seat is in a position of use,
      a rear engaging portion which extends rearwardly from said retaining portion to terminate at a rearwardly facing wall,
      a surrounding sealing flange which extends from said rearwardly facing wall radially and outwardly to be in fluid-tight engagement with said rear surface segment, and which extends forwardly to terminate at a surrounding flange surface that is movable towards said second friction diminishing region in the longitudinal direction, said rear engaging portion having an inner tubular wall surface which surrounds the axis to define a cavity that extends from said rearwardly facing wall towards said front engaging portion and that terminates at a ceiling wall, said ceiling wall having an axial hole which establishes a fluid communication between said needle cannula and said cavity, and
      a radially yieldable catch which is disposed on said inner tubular wall surface distal from said ceiling wall, and which is yieldable radially and outwardly in response to a kinetic frictional force; and
   a plunger disposed to be movable in said passage along said rear surface segment, and having a front end wall, an engaging head which is opposite to said front end wall in the longitudinal direction, a neck which is interposed between said engaging head and said front end wall, and which is of a dimension such that a rearwardly facing shoulder wall is formed between said engaging head and said neck, and such that the kinetic frictional force is generated as a result of axial movement of said engaging head relative to said radially yieldable catch towards said ceiling wall, and a deformable sealing member which is sleeved on said engaging head and said neck, which is in frictional engagement with said engaging head with a second frictional force, and which is sealingly slidable relative to said rear surface segment such that,
   in the position of use, said deformable sealing member is moved forward by virtue of forward movement of said plunger to abut against said rearwardly facing wall, while said engaging head is extended into said cavity, and such that,
   when said plunger is to be placed in a disposal position, said engaging head is kept moving towards said ceiling wall by a pushing force which is applied to said plunger, and which, when said deformable sealing member is blocked by said rearwardly facing wall from moving with said engaging head, overcomes the second frictional force, thereby exposing said neck so as to permit said rearwardly facing shoulder wall to be forced to slip over said radially yieldable catch and to be retained by said radially yieldable catch such that said rearwardly facing shoulder wall is prevented from moving rearwardly, said engaging head and said inner tubular wall surface being configured such that, after said rearwardly facing shoulder wall has slipped over said radially yieldable catch, continued movement of said engaging head towards said ceiling wall, against the first frictional force, forces said retaining portion and said surrounding sealing flange to move into said first and second friction diminishing regions, respectively, so as to facilitate a subsequent pulling action of said plunger whereby said needle seat is brought towards said rear open end by virtue of the retention of said rearwardly facing shoulder wall by said radially yieldable catch, thereby retracting said needle cannula into said passage.

2. The disposable syringe of claim 1, wherein said needle seat is disposed to be in splined engagement with said engaging head such that once said rearwardly facing shoulder wall is retained by said radially yieldable catch, and once said retaining portion and said surrounding sealing flange are moved into said first and second friction diminishing regions, respectively, said needle seat is enabled to be rotated with said plunger to thereby further diminish friction between said needle seat and said inner wall surface so as to facilitate the subsequent pulling action of said plunger.

3. The disposable syringe of claim 2, wherein said needle seat has a plurality of axially extending ribs which are formed on said inner tubular wall surface proximate to said ceiling wall and which are angularly displaced from one another about the axis, said engaging head having a plurality of axially extending grooves formed to mate with said axially extending ribs so as to bring said needle seat into the splined engagement with said engaging head.

4. The disposable syringe of claim 1, wherein said front engaging portion has a filling hole filled with an adhesive to affix said needle cannula to said front engaging portion.

5. The disposable syringe of claim 1, wherein said intermediate surface segment has a shoulder abutment which is disposed between said retaining region and said second friction diminishing region to permit abutment of said surrounding flange surface thereagainst immediately after said surrounding sealing flange is moved into said second friction diminishing region.

6. The disposable syringe of claim 1, wherein said retaining region extends radially and outwardly to form an annular recess, said needle seat having a protrusion formed on said retaining portion so as to be retained in said recess by virtue of the first frictional force.

7. The disposable syringe of claim 6, wherein said retaining portion has a plurality of fins which are angularly displaced from one another about the axis and which are spaced apart from said first friction diminishing region radially, each of said fins being configured such that a contour constituted by said fins about the axis serves as said protrusion.

8. The disposable syringe of claim 1, wherein said front surface segment is configured to converge toward said front open end to prevent removal of said needle seat from said front open end.

9. The disposable syringe of claim 1, wherein said surrounding barrel wall has an outer wall surface which has a rib portion extending in the longitudinal direction and disposed adjacent to said front open end, said disposable syringe further comprising a tip protector which is disposed to sleeve on said outer wall surface, and which is frictionally retained by said rib portion for shielding said needle cannula.

10. The disposable syringe of claim 1, wherein said surrounding barrel wall has an outer wall surface which has an annular step portion that faces forwardly, and that is distal from said front open end, and a surrounding front segment interposed between said front open end and said annular step portion, said disposable syringe further comprising
    a catheter hub including a surrounding hub wall which has a sleeve portion that is sleeved on said surrounding front segment and that has a terminal edge abutting against said step portion, and a tip portion opposite to said sleeve portion along the axis; and
    a tubular catheter including a proximate segment which is disposed in said tip portion and which extends along the axis, and a distal segment which extends from said proximate segment along the axis to project outwardly of said tip portion.

11. The disposable syringe of claim 1, wherein said front engaging portion has a seat segment which is configured to extend outwardly of said barrel from said front open end when said needle seat is in the position of use.

12. The disposable syringe of claim 11, further comprising a tip protector which is disposed to sleeve on and which is frictionally retained to said seat segment of said front engaging portion for shielding of said needle cannula.

13. The disposable syringe of claim 11, wherein said front engaging portion further has a hub segment which is configured to fix said needle cannula along the axis, and which is sleeved on said seat segment to establish fluid communication between said needle cannula and said axial hole.

14. The disposable syringe of claim 13, further comprising
    a catheter hub including a surrounding hub wall which has a sleeve portion that is sleeved on said hub segment, and a tip portion opposite to said sleeve portion along the axis; and
    a tubular catheter including a proximate segment which is disposed in said tip portion and which extends along the axis, and a distal segment which extends from said proximate segment along the axis and outwardly of said tip portion.

15. The disposable syringe of claim 11, wherein said retaining region has a plurality of recesses which are angularly displaced from one another about the axis,
    said intermediate surface segment further having a plurality of barriers which are angularly displaced from one another about the axis,
    said retaining portion of said needle seat having a plurality of partitions which are angularly displaced from one another about the axis, and a plurality of blocking segments which respectively extend from said partitions radially and outwardly, each of said blocking segments being configured such that when said needle seat is brought to be inserted into said passage from said rear open end, and immediately after each of said partitions is brought to pass between two adjacent ones of said barriers, each of said partitions is turned a predetermined angle in one of clockwise and counterclockwise directions such that each of said blocking segments is received in and is engaged with a respective one of said recesses by virtue of the first frictional force, while being prevented by one of said two adjacent ones of said barriers from axial movement relative to said second diminishing region, thereby placing said needle seat firmly in the position of use.

16. The disposable syringe of claim 15, wherein said retaining region has a plurality of bumps respectively extending from said recesses inwardly and radially such that when said partitions are turned the predetermined angle in a corresponding one of the counterclockwise and clockwise directions, said blocking segments slip over said bumps respectively so that the user is aware of movement of said blocking segments to a position where said blocking segments are unrestrained by said barriers and are permitted to perform axial movement.

17. The disposable syringe of claim 1, wherein said deformable sealing member is disposed to be spaced apart from said front end wall so as to permit relative movement of said deformable sealing member towards said front end wall when the pushing force is applied to overcome the second frictional force.

18. The disposable syringe of claim 1, further comprising an O-ring which is disposed on said needle seat, which surrounds the axis, and which is configured to enhance fluid-tightness of the engagement between said front surface segment and said front engaging portion, or between said rear surface segment and said surrounding sealing flange.

* * * * *